US010475526B2

(12) United States Patent
Jones et al.

(10) Patent No.: US 10,475,526 B2
(45) Date of Patent: Nov. 12, 2019

(54) SYSTEMS, APPARATUS, AND METHODS FOR GENERATING AND ANALYZING RESISTOME PROFILES

(71) Applicant: OpGen, Inc., Gaithersburg, MD (US)

(72) Inventors: Evan Jones, Potomac, MD (US); Vadim Sapiro, North Potomac, MD (US); George Terrance Walker, Chevy Chase, MD (US); Alex Saeed, Germantown, MD (US)

(73) Assignee: OpGen, Inc., Gaithersburg, MD (US)

( * ) Notice: Subject to any disclaimer, the term of this patent is extended or adjusted under 35 U.S.C. 154(b) by 0 days.

(21) Appl. No.: 14/723,424

(22) Filed: May 27, 2015

(65) Prior Publication Data

US 2016/0085912 A1  Mar. 24, 2016

Related U.S. Application Data

(60) Provisional application No. 62/033,351, filed on May 27, 2014, provisional application No. 62/004,026, filed on May 28, 2014, provisional application No. 62/024,322, filed on Jul. 14, 2014.

(51) Int. Cl.
| | |
|---|---|
| *G01N 33/48* | (2006.01) |
| *G16B 40/00* | (2019.01) |
| *G16B 20/00* | (2019.01) |
| *G16B 45/00* | (2019.01) |
| *G06G 7/58* | (2006.01) |

(52) U.S. Cl.
CPC ............ *G16B 40/00* (2019.02); *G16B 20/00* (2019.02); *G16B 45/00* (2019.02)

(58) Field of Classification Search
None
See application file for complete search history.

(56) References Cited

U.S. PATENT DOCUMENTS

| | | |
|---|---|---|
| 2009/0163382 A1 | 6/2009 | Oh et al. |
| 2011/0151458 A1 | 6/2011 | Garaizar Candina et al. |
| 2013/0183679 A1 | 7/2013 | Ploy et al. |
| 2015/0259729 A1 | 9/2015 | Walker et al. |
| 2017/0253917 A1 | 9/2017 | Walker et al. |

FOREIGN PATENT DOCUMENTS

| | | |
|---|---|---|
| CN | 102899414 A | 1/2013 |
| WO | WO 2010/039763 A2 | 4/2010 |
| WO | WO 2011/138402 A1 | 11/2011 |
| WO | WO 2012/032158 A1 | 3/2012 |
| WO | WO 2012106432 A2 | 9/2012 |
| WO | WO 2013/117746 A1 | 8/2013 |
| WO | WO 2013/163210 A1 | 10/2013 |
| WO | WO 2015/114094 A1 | 8/2015 |
| WO | WO 2015/138991 A2 | 9/2015 |
| WO | WO 2015/184017 A1 | 12/2015 |

OTHER PUBLICATIONS

Search Report and Written Opinion for International Patent Application No. PCT/US2015/032761 dated Sep. 14, 2015.
Espedido, et al., "Whole Genome Sequence Analysis of the First Australian OXA-48-Producing Outbreak-Associated Klebsiella pneumoniae Isolates: The Resistome and In Vivo Evolution." PLoS One (2013); 8(3): e59920: 1-6.
Hasman, et al., "Rapid whole genome sequencing for the detection and characterization of microorganisms directly from clinical samples." Journal of Clinical Microbiology (2013); 52(1): 139-146.
International Preliminary Report on Patentability for International Patent Application No. PCT/US2015/032761 dated Nov. 29, 2016, 10 pages.
Robinson, et al., "Genomics and outbreak investigation: from sequence to consequence." Genome Medicine (2013); 5: 36, 9 pages.
Snitkin, et al., "Tracking a Hospital Outbreak of Carbapenem-Resistant Klebsiella pneumoniae with Whole-Genome Sequencing." Science Translational Medicine (2012); 4(148): pp. 148ra116, 11 pages.
Agyekum, A. et al. "Predictability of Phenotype in Relation to Common [beta]-Lactam Resistance Mechanisms in *Escherichia coli* and Klebsiella pneumonia", Journal of Microbiology (2016); 54(5): 1243-1250.
Aitmhand et al., "Plasmid-mediated TEM-3 extended-spectrum β-lactamase production in *Salmonella typhimurium* in Casablanca.", J Antimicrob Chemother (2002), 49: 169-172.
Arnold et al., "Emergence of Klebsiella pneumoniae Carbapenemase (KPC)-Producing Bacteria", South Med J (2011), 104: 40-45.
Bahar et al., "Detection of VIM-5 metallo-β-lactamase in a Pseudomonas aeruginosa clinical isolate from Turkey", J Antimicrob Chemother (2004), 54: 282-283.
Barnaud et al., "*Salmonella enteritidis*: AmpC Plasmid-Mediated Inducible β-Lactamase (DHA-1) with an ampR Gene from Morganella morganii", Antimicrob Agents Chemother (1998), 42: 2352-2358.
Bauernfeind et al., "A Novel Type of AmpC β-Lactamase, ACC-1, Produced by a Klebsiella pneumoniae Strain Causing Nosocomial Pneumonia", Antimicrob Agents Chemother (1999), 43: 1924-1931.
Bauernfeind et al., "Characterization of the Plasmidic β-Lactamase CMY-2, Which Is Responsible for Cephamycin Resistance", Antimicrob Agents Chemother (1996), 40: 221-224.

(Continued)

*Primary Examiner* — Eric S Dejong
(74) *Attorney, Agent, or Firm* — Cooley LLP

(57) ABSTRACT

Systems, apparatus, and methods are disclosed for generating a resistome profile for a subject, monitoring an infection state of one or more subjects, and/or identifying a potential infection outbreak at a facility, for example, by obtaining first data representative of at least one measure of antibiotic resistance of an organism from a first sample, identifying the organism, determining at least one of an antibiotic susceptibility phenotype, an identity of an antibiotic resistance gene, and an antibiotic to which the organism is non-susceptible, generating and comparing a first pattern to at least one known pattern to determine and generate a profile uniqueness identifier indicating a degree of similarity above a threshold between the first pattern and the at least one known pattern.

26 Claims, 10 Drawing Sheets

(56) References Cited

OTHER PUBLICATIONS

Bauernfeind et al., "Comparative Characterization of the Cephamycinase blaCMY-1 Gene and Its Relationship with Other b-Lactamase Genes", Antimicrob Agents Chemother (1996), 40: 1926-1930.
Berrazeg et al., "New Delhi Metallo-β-Lactamase Around the World: An eReview Using Google Maps", Eurosurveillance (2014), 19: 1-14.
Bhattacharya, "Early diagnosis of resistant pathogens. How can it improve antimicrobial treatment?" Virulence (2013); 4 (2):172-184.
Bonnet et al., "A Novel Class A Extended-Spectrum β-Lactamase (BES-1) in Serratia marcescens Isolated in Brazil", Antimicrob Agents Chemother (2000), 44: 3061-3068.
Bou et al., "OXA-24, a Novel Class D β-Lactamase with Carbapenemase Activity in an Acinetobacter baumannii Clinical Strain", Antimicrob Agents Chemother (2000), 44: 1556-1561.
Bradford et al., "Imipenem Resistance in Klebsiella pneumoniae is Associated with the Combination of ACT-1, a Plasmid-Mediated AmpC β-Lactamase, and the Loss of an Outer Membrane Protein", Antimicrob Agents Chemother (1997), 41: 563-569.
Bradley P. et al. "Rapid antibiotic-resistance predictions from genome sequence data for *Staphylococcus aureus* and *Mycobacterium tuberculosis*", Nature Communications (2015); 6: 10063, and Corrigendum, 15 pages.
Castanheira et al., "Molecular characterization of a β-Lactamase Gene, blaGIM-1, encoding a new subclass of Metallo-β-Lactamase", Antimicrob Agents Chemother (2004), 48: 4654-4661.
Chaves et al., "SHV-1 β-Lactamase is Mainly a Chromosomally Encoded Species-Specific Enzyme in Klebsiella pneumoniae", Antimicrob Agents Chemother (2001), 45: 2856-2861.
Cook, Nancy R. "Use and misuse of the receiver operating characteristic curve in risk prediction." Circulation (2007); 115.7: 928-935.
Corkill et al., "SHV-27, A Novel Cefotaxime-Hydrolysing β-Lactamase, Identified in Klebsiella pneumoniae isolates from a Brazilian hospital", Journal of Antimicrobial Chemotherapy (2001), 47: 463-465.
Crowley et al., "Expression of SHV-2 β-Lactamase and of Reduced Amounts of β-OmpK36 Porin in Klebsiella pneumoniae Results in Increased Resistance to Cephalosporins and Carbapenems", Antimicrob Agents Chemother (2002), 46: 3679-3682.
Da Silva et al., "Molecular Characterization of blaIMP-5, a New Integron-Borne Metallo-β-lactamase Gene from an Acinetobacter baumannii Nosocomial Isolate in Portugal", FEMS Microbiology Letters (2002), 215: 33-39.
Dalla-Costa et al., "Outbreak of Carbapenem-Resistant Acinetobacter baumannii Producing the OXA-23 Enzyme in Curitiba, Brazil", J Clin Micro (2003), 41 (7): 3403-3406.
Danel et al., "OXA-15, an Extended-Spectrum Variant of OXA-2 β-Lactamase, Isolated from a Pseudomonas aeruginosa Strain", Antimicrob Agents Chemother (1997), 41: 785-790.
Fonseca et al., "Biochemical Characterization of SFC-1, a Class A Carbapenem-Hydrolyzing β-Lactamase", Antimicrob Agents Chemother (2007), 51: 4512.
Francis, R.O., et al., "Rapid Detection of Klebsiella pneumoniae Carbapenemase Genes in Enterobacteriaceae Directly From Blood Culture Bottles by Real-Time PCR." American Journal of Clinical Pathology (2012); 137(4): 627-632.
Girlich et al., "Biochemical Characterization of the Naturally Occurring Oxacillinase OXA-50 of Pseudomonas aeruginos," Antimicrob Agents Chemother (2004a), 48: 2043-2048.
Girlich et al., "OXA-60, a Chromosomal, Inducible, and Imipenem-Hydrolyzing Class D β-Lactamase from Ralstonia pickettii", Antimicrob Agents Chemother (2004b), 48: 4217-4225.
Gutmann et al., "Plasmid-Mediated Beta-Lactamase (TEM-7) Involved in Resistance to Ceftazidime and Aztreonam", Rev Infect Dis (1988), 10: 860-866.
Gutmann et al., "SHV-5, a Novel SHV-Type r-Lactamase that Hydrolyzes Broad-Spectrum Cephalosporins and Monobactams", Antimicrob Agents Chemother (1989), 33 (6): 951-956.

Héritier et al., "Genetic and Biochemical Characterization of a Chromosome-Encoded Carbapenem-Hydrolyzing Ambler Class D β-Lactamase from Shewanella algae", Antimicrob Agents Chemother (2004), 48: 1670-1675.
Horii et al., "Characterization of a Plasmid-Borne and Constitutively Expressed blaMOX-1 Gene Encoding AmpC-Type b-Lactamase", Gene (1994), 139: 93-98.
International Preliminary Report on Patentability, PCT/US2015/020590, dated Sep. 13, 2016, 10 pages.
International Search Report and Written Opinion for International Application No. PCT/US2017/021209, dated May 29, 2017, 15 pages.
International Search Report, PCT/US2015/020590, dated Sep. 18, 2015, 9 pages.
Jeong et al., "Molecular Characterization of Extended-Spectrum Beta-Lactamases Produced by Clinical Isolates of Klebsiella pneumoniae and *Escherichia coli* from a Korean Nationwide Survey", J Clinic Microb (2004), 42: 2902-2906.
Jordana-Lluch et al. "Rapid Diagnosis of Bloodstream Infections with PCR Followed by Mass Spectrometry," PLOS ONE, vol. 8, No. 4, Apr. 23, 2013, p. e62108.
Juan et al., "Characterization of the New Metallo-β-Lactamase VIM-13 and Its Integron-Borne Gene from a Pseudomonas aeruginosa Clinical Isolate in Spain", Antimicrob Agents Chemother (2008), 52: 3589-3596.
Koh et al., "Carbapenem-Resistant Klebsiella pneumoniae in Singapore Producing IMP-1 β-Lactamase and Lacking an Outer Membrane Protein", Antimicrob Agents Chemother (2001), 45: 1939-1940.
Kos, V. N. et al. "The Resistome of Pseudomonas aeruginosa in Relationship to Phenotypic Susceptibility", Antimicrobial Agents and Chemotherapy (2015); 59(1): 427-436.
Lakshmi et al., "Role of Beta-Lactamases in Antibiotic Resistance: a Review", Int Res J Pharm (2014), 5 (2): 37-40.
Lee et al., "Novel Acquired Metallo-β-Lactamase Gene, blaSIM-1, in a Class 1 Integron from Acinetobacter baumannii Clinical Isolates from Korea", Antimicrob Agents Chemother (2005), 49: 4485-4491.
Llop, P., et al., "Development of a Highly Sensitive Nested-PCR Procedure Using a Single Closed Tube for Detection of Erwinia amylovora in Asymptomatic Plant Material." Appl Environ Microbiol. (2000); 66(5): 2071-2078.
Lupo et al. "Non-phenotypic tests to detect and characterize antibiotic resistance mechanisms in Enterobacteriaceae," Diagnostic Microbiology and Infectious Diseases (2013); 77(3): 179-194.
Matsumoto et al., "Characterization of SFO-1, A Plasmid-Mediated Inducible Class A β-Lactamase from Enterobacter cloacae", Antimicrob Agents Chemother (1999), 43: 307-313.
Mazzariol et al., "Detection of a New SHV-Type Extended-Spectrum β-Lactamase, SHV-31, in a Klebsiella pneumoniae Strain Causing a Large Nosocomial Outbreak in the Netherlands", Antimicrob Agents Chemother (2007), 51: 1082-1084.
Menezes et al. "Diagnosis by real-time polymerase chain reaction of pathogens and antimicrobial resistance genes in bone marrow transplant patients with bloodstream infections." BMC Infectious Diseases (2013); 13 (1): 166.
Miró et al., "*Escherichia coli* Producing an ACC-1 Class C β-Lactamase Isolated in Barcelona, Spain", Antimicrob Agents Chemother (2005), 49 (2): 866-867.
Monteiro et al. "Rapid detection of carbapenemase genes by multiplex real-time PCR," Journal of Antimicrobial Chemotherapy (2012); 67: 906-909.
Mossakowska et al., "Oxacillin-Hydrolysing β-Lactamases, A Comparative Analysis at Nucleotide and Amino Acid Sequence Levels", Eur J Biochem (1989), 180: 309-318.
Mugnier et al., "A TEM-Derived Extended-Spectrum β-Lactamase in Pseudomonas aeruginosa", Antimicrob Agents Chemother (1996), 40 (11): 2488-2493.
Mulvey et al., "Ambler Class A Extended-Spectrum Beta-Lactamase-Producing *Escherichia coli* and *Klebsiella* spp. in Canadian Hospitals", Antimicrob Agents Chemother (2004), 48 (4): 1204-1214.
Naas et al., "Identification of CTX-M-Type Extended-Spectrum-β-Lactamase Genes Using Real-Time PCR and Pyrosequencing", Antimicrob Agents Chemother (2007), 51 (1): 223-230.

(56) References Cited

OTHER PUBLICATIONS

Naas et al., "Minor Extended-Spectrum β-Lactamases", Clin Microbiol Infect (2008), 14: 42-52.
Naas and Nordmann., "Oxa-Type β-Lactamases", Current Pharmaceutical Design (1999), 5: 865-879.
Nakano et al., "CFE-1, A Novel Plasmid-Encoded AmpC β-Lactamase with an ampR Gene Originating from Citrobacter freundii", Antimicrob Agents Chemother (2004), 48 (4): 1151-1158.
Nordmann and Naas, "Sequence Analysis of PER-1 Extended-Spectrum β-Lactamase from Pseudomonas aeruginosa and Comparison with Class A β-Lactamases", Antimicrob Agents Chemother (1994), 38 (1): 104-114.
O'Marcaigh, Aengus S., and Jackson, Robert M. "Estimating the predictive value of a diagnostic test: how to prevent misleading or confusing results." Clinical Pediatrics (1993); 32.8: 485-491.
Opazo et al., "OXA-Type Carbapenemases in Acinetobacter baumannii in South America", J Infect Dev Ctries (2012), 6 (4): 311-316.
Papanicolaou et al., "Novel Plasmid-Mediated β-Lactamase (MIR-1) Conferring Resistance to Oxyimino- and α-Methoxy β-Lactams in Clinical Isolates of Klebsiella pneumoniae", Antimicrob Agents Chemother (1990), 34 (11): 2200-2209.
Pepe, Margaret Sullivan, et al. "Limitations of the odds ratio in gauging the performance of a diagnostic, prognostic, or screening marker." American Journal of Epidemiology (2004); 159.9: 882-890.
Perilli et al., "Characterization of a New Extended-Spectrum β-Lactamase (TEM-87) Isolated in Proteus mirabilis during an Italian Survey", Antimicrob Agents Chemother (2002), 46 (3): 925-928.
Philippon et al., "OXA-18, a Class D Clavulanic Acid-Inhibited Extended-Spectrum β-Lactamase from Pseudomonas aeruginosa", Antimicrob Agents Chemother (1997), 41 (10): 2188-2195.
Philippon et al., "Plasmid-Determined AmpC-Type β-Lactamases." Antimicrob Agents Chemother (2002), 46 (1): 1-11.
Poirel et al., "BEL-1 a Novel Clavulanic Acid-Inhibited Extended-Spectrum β-lactamase, and the Cass 1 Integron In120 in Pseudomonas aeruginosa", Antimicrob Agents Chemother (2005a), 49(9): 3743-3748.
Poirel et al., "Biochemical Sequence Analyses of GES-1, A Novel class A Extended Spectrum β-Lactamase, and the Class 1 Integron In52 from Klebsiella pneumoniae", Antimicrob Agents Chemother (2000), 44 (3): 622-632.
Poirel et al., "Chromosome-Encoded Ambler Class D β-Lactamase of Shewanella oneidensis as a Progenitor of Carbapenem-Hydrolyzing Oxacillinase", Antimicrob Agents Chemother (2004b), 48 (1): 348-351.
Poirel et al., "Emergence of Oxacillinase-Mediated Resistance to Imipenem in Klebsiella pneumoniae", Antimicrob Agents Chemother (2004a), 48 (1): 15-22.
Poirel et al., "Integron-Located oxa-32 Gene Cassette Encoding an Extended-Spectrum Variant of OXA-2 β-Lactamase from Pseudomonas aeruginosa", Antimicrob Agents Chemother (2002), 46 (2): 566-569.
Poirel et al., "Molecular and Biochemical Characterization of VEB-1, A Novel Class A Extended-Spectrum β-Lactamase Encoded by an *Escherichia coli* Integron Gene", Antimicrob Agents Chemother (1999), 43 (3): 573-581.
Poirel et al., "OXA-58, A Novel Class D β-Lactamase Involved in Resistance to Carbapenems in Acinetobacter baumannii", Antimicrob Agents Chemother (2005b), 49 (1): 202-208.
Pottumarthy et al., "NmcA Carbapenem Hydrolyzing Enzyme in Enterobacter cloacae in North America", Emerging Infectious Diseases (2003), 9: 999-1002.
Queenan et al., "SME-Type Carbapenem-Hydrolyzing Class Diverse Serratia marcescens Strains A β-Lactamases from Geographically diverse Serratia marcescens strains", Antimicrob Agents Chemother (2000), 44 (11): 3035-3039.
Quinn et al., "Novel Plasmid-Mediated β-Lactamase (TEM-10) Conferring Selective Resistance to Ceftazidime and Aztreonam in Clinical Isolates of Klebsiella pneumoniae", Antimicrob Agents Chemother (1989), 33 (9): 1451-1456.
Raghunath et al., "New metallo β-lactamase NDM-1", Indian J Med Res (2010), 132 (5): 478-481.
Rampersad, J.N., et al., "A nested-PCR with an Internal Amplification Control for the detection and differentiation of Bartonella henselae and B. clarridgeiae: an examination of cats in Trinidad." BMC Infect Dis. (2005); 5: 63.
Rasmussen et al., "Characterization of IMI-1 β-Lactamase, a Class A Carbapenem-Hydrolyzing Enzyme from Enterobacter cloacae", Antimicrob Agents Chemother (1996), 40 (9): 2080-2086.
Sacha et al., "The KPC Type β-Lactamases: New Enzymes that Confer Resistance to Carbapenems in Gram-negative Bacilli", Folia Histochemica Et Cytobiologica (2009), 47 (4): 537-543.
Schneider et al., "Novel Carbapenem-Hydrolyzing Oxacillinase OXA-62 from Pandoraea pnomenusa", Antimicrob Agents Chemother (2006), 50: 1330-1335.
Singapore Application No. 11201607588W, Written Opinion dated Oct. 19, 2017, 3 pages.
Singapore Application No. 11201609867V, Written Opinion dated Oct. 27, 2017, 7 pages.
Shultz, "Clinical Interpretation of Laboratory Procedures," Chapter 14 in Teitz, Fundamentals of Clinical Chemistry, Burtis and Ashwood (eds.), 4th edition 1996, W.B. Saunders Company, pp. 192-199.
Silva et al., "TLA-1: A New Plasmid-Mediated Extended-Spectrum β-Lactamase from *Escherichia coli*", Antimicrob Agents Chemother (2000), 44 (4): 997-1003.
Stoesser, N., et al. "Predicting antimicrobial susceptibilities for *Escherichia coli* and Klebsiella pneumoniae isolates using whole genomic sequence data", Journal of Antimicrobial Chemotherapy (2013); 68 (10): 2234-2244.
Suzuki et al. "Supplementary information. Supplementary Figures", Nature Methods, 2014, 14 pages. Retrieved from the Internet: URL:https://www.nature.com/article-assets/npg/ncomms/2014.
Suzuki, S. et al. "Prediction of antibiotic resistance by gene expression profiles", Nature Communications (2014); 5: 5792.
Swick, M.C. et al. "Novel Conserved Genotypes Correspond to Antibiotic Resistance Phenotypes of *E. coli* Clinical Isolates", PLOS ONE (2013); 8(6): e65961.
Taneja et al., "High Occurrence of blaCMY-1 AmpC Lactamase Producing *Escherichia coli* in Cases of Complicated Urinary Tract Infection (UTI) from a Tertiary Health Care Centre in North India", Indian J Med Res (2000), 136 (2): 289-291.
Toleman et al., "blaNim7 Evolutionarily Distinct Metallo-β-Lactamase Gene in a Pseudomonas aeruginosa Isolate from the United States", Antimicrob Agents Chemother (2004), 48 (1): 329-332.
Toleman et al., "Molecular and Biochemical Characterization of OXA-45, an Extended-Spectrum Class 2d' β-Lactamase in Pseudomonas aeruginosa", Antimicrob Agents Chemother (2003), 47 (9): 2859-2863.
Toleman et al., "Molecular characterization of SPM-1, A Novel Metallo-β-Lactamasel solated in Latin America: Report from the SENTRY Antimicrobial Surveillance Programme", Journal of Antimicrobial Chemotherapy (2002), 50 (5): 673-679.
Vahaboglu et al., "High Prevalence of OXA-51-Yype class D β-Lactamases Among Ceftazidime-Resistant Clinical lisolates of *Acinetobacter* spp.: Co-Existence with OXA-58 in Multiple Centres", J Antimicrob Chemother (2006), 58 (3): 537-542.
Walsh et al., "Metallo-β-Lactamases: the Quiet before the Storm?", Clin Microbiol Rev (2005), 18 (2): 306-325.
Written Opinion, PCT/US2015/020590, dated Sep. 18, 2015, 9 pages.
Yigit et al., "Novel Carbapenem-Hydrolyzing β-Lactamase, KPC-1, from a Carbapenem-Resistant Strain of Klebsiella pneumoniae", Antimicrob Agents Chemother (2001), 45 (4): 151-1161.
Yong et al., "Characterization of a New Metallo-β-Lactamase Gene, blaNDM-1, and a Novel Erythromycin Esterase Gene Carried on a Unique Genetic Structure in Klebsiella pneumoniae Sequence Type 14 from India", Antimicrob Agents Chemother (2009), 53 (12): 5046-5054.
Zweig, Mark H., et al. "ROC curve analysis: an example showing the relationships among serum lipid and apolipoprotein concentra-

(56) References Cited

OTHER PUBLICATIONS tions in identifying patients with coronary artery disease." Clinical Chemistry (1992); 38.8: 1425-1428.
U.S. Appl. No. 14/657,908, Office Action dated Nov. 7, 2016, 23 pages.
U.S. Appl. No. 14/657,908, Office Action dated Jul. 3, 2017, 29 pages.
U.S. Appl. No. 14/657,908, Office Action dated Feb. 5, 2018, 29 pages.

SYSTEMS, APPARATUS, AND METHODS FOR GENERATING AND ANALYZING RESISTOME PROFILES

CROSS-REFERENCE TO RELATED APPLICATIONS

The present application claims a priority benefit to U.S. provisional patent application Ser. No. 62/024,322, entitled "Analysis Platform Based on Resistome Profiles," filed on Jul. 14, 2014, which is incorporated herein by reference in its entirety.

The present application also claims a priority benefit to U.S. provisional patent application Ser. No. 62/004,026, entitled "Systems and Methods for Infection Control and Patient Management," filed on May 28, 2014, which is incorporated herein by reference in its entirety.

The present application also claims a priority benefit to U.S. provisional patent application Ser. No. 62/003,351, entitled "Systems and Methods for Infection Control and Patient Management," filed on May 27, 2014, which is incorporated herein by reference in its entirety.

TECHNICAL FIELD

The present disclosure relates generally to monitoring multi-gene resistant colonization and infection in subjects and potential for outbreaks at facilities. More specifically, the present disclosure relates to generating and using resistome profiles based on measurements of biological samples.

BACKGROUND

Antibiotic-resistant bacterial infections are associated with poor clinical outcomes including increased morbidity, mortality, and healthcare costs among infected patients.

Colonized patients are an important reservoir of beta-lactamases leading to the transmission and spread of these organisms within hospitals and long term care facilities. The prevalence of these organisms in such facilities in the United States has steadily increased over the last 30 years. Treatment options for patients with multi-drug resistant organisms (MDROs) are extremely limited; therefore, identification of infection and containment of any potential outbreak within facilities is crucial.

SUMMARY

The inventors have recognized and appreciated that an ultra-sensitive method for generating a resistome profile for a subject based on measurements of biological samples and monitoring the multi-gene resistant colonization and infection in subjects could be beneficial, for example, for identification of potentially dangerous infections. The inventors have also recognized that methods for identifying a potential for an infection outbreak at a facility could be beneficial for containment of any such potential outbreak. In view of the foregoing, various embodiments herein are directed generally to systems, apparatus, and methods for generating a resistome profile for a subject, monitoring the infection state of one or more subjects, and/or identifying a potential for an infection outbreak at a facility.

According to some embodiments, systems, apparatus, and methods of the instant disclosure provide a dynamic way to identify, categorize, consolidate, compare, manage, and make predictions from different classes of diagnostic information relevant to infections and outbreaks, particularly by drug resistant organisms. The systems, apparatus, and methods may rely on diagnostically useful information based on phenotype information, genotype information, or some combination thereof. For example, genetic analysis of DNA or RNA sequence information or matches thereof may be used to identify organisms such as E. coli b0507, which is known to be a pathogenic strain of bacteria. Beyond looking at single types of organisms, in some embodiments, systems, methods and apparatus provide for subject classification, infection state classification, facility classification, and outbreak monitoring based on analysis of the multi-drug resistance of organisms.

The present disclosure provides systems, methods and apparatus for generating a resistome profile for a subject according to some embodiments. In one embodiment, a system for generating a resistome profile includes at least one communication interface, at least one memory for storing processor executable instructions, and at least one processor, communicatively coupled to the at least one communication interface and the at least one memory. Upon execution of the processor-executable instructions, the at least one processor obtains first data representative of at least one measure of antibiotic resistance of an organism from a first sample, identifies the organism based on at least the first data, determines at least one of an antibiotic susceptibility phenotype, an identity of an antibiotic resistance gene, and an antibiotic to which the organism is non-susceptible based on at least the first data, and generates a first pattern associated with the first sample. The first pattern includes an organism identification code indicating the organism identified based on the first data and at least one of a phenotype code indicating the antibiotic susceptibility phenotype determined from the first data, a genotype code indicating the identity of the antibiotic resistance gene determined from the first data, and a susceptibility code indicating the antibiotic to which the organism is non-susceptible determined from the first data. The at least one processor also compares the first pattern to at least one known pattern, determines a degree of similarity above a threshold between the first pattern and the at least one known pattern, generates a profile uniqueness identifier indicating the degree of similarity above the threshold between the first pattern and the at least one known pattern, and generates a first resistome profile based on at least the first pattern and the profile uniqueness identifier.

In an embodiment, the first pattern includes a plurality of genotype codes, each genotype code indicating the identity of a different antibiotic resistance gene. The profile uniqueness identifier may include a uniqueness code determined based on the degree of similarity above the threshold between the first pattern and the at least one known pattern and a repetition index indicating an increase in a number of known patterns having the degree of similarity above the threshold with the first pattern. The at least one processor may compare the first pattern to the at least one known pattern by applying a similarity metric to the first pattern and the at least one known pattern to determine the degree of similarity above the threshold between the first pattern and the at least one known pattern.

In an embodiment, the first sample is obtained from at least one of an anal swab, a rectal swab, a skin swab, nasal swab, wound swab, stool, blood, plasma, serum, urine, sputum, respiratory lavage, and cerebrospinal fluid. The first data representative of the at least one measure of antibiotic resistance of the organism from the first sample may include data representative of at least one of a type of gene, a gene sequence, a gene family, a DNA sequence, a single-nucleotide polymorphism, a type of nucleic acid, a type of protein, and a protein expression. The first resistome profile further may include metadata associated with at least one of the first sample and a first subject from which the first sample was obtained. The first data representative of the at least one measure of antibiotic resistance of the organism from the first sample may include data representative of at least one measure of a susceptibility test performed on a first bacterial isolate from the first sample.

In an embodiment, the system further includes a graphical display communicatively coupled to the at least one processor. Upon execution of the processor-executable instructions, the at least one processor may display the first resistome profile using a graphical representation. The graphical representation may include a quick response (QR) code, a tube graph, and/or an epidemiology star chart.

In an embodiment, the first data representative of the at least one measure of antibiotic resistance of the organism from the first sample is collected from at least one measurement of a first bacterial isolate from the first sample and indicates at least one of an antibiotic resistance of the first bacterial isolate and an antibiotic susceptibility of the first bacterial isolate. The at least one known pattern may be derived from measurement data associated with a second bacterial isolate from a second sample obtained from at least one of a colonized subject and an infected subject, the colonized patient having tested positive for at least one drug-resistant organism, and the infected patient having at least one of a central line blood infection, ventilator associated pneumonia, a urinary tract infection, and a surgical site infection, the measurement data indicating at least one of an antibiotic resistance of the first bacterial isolate and an antibiotic susceptibility of the first bacterial isolate. The first data representative of the at least one measure of antibiotic resistance of the organism from the first sample may indicate at least one of a genome sequence, a minimum inhibitory concentration for an antibiotic, and MALDI-TOF data. The first data representative of the at least one measure of antibiotic resistance of the organism from the first sample may include in silico data from a reference organism involved in an outbreak.

In one embodiment, a method includes providing a first data representative of at least one measure of antibiotic resistance of an organism, from a sample obtained from a first subject, and generating a first pattern associated with the first subject. The first pattern includes an organism identification code indicating the identity of the organism identified based on the first data. The first pattern also includes at least one of: a phenotype code based on an antibiotic susceptibility phenotype determined from the first data, a genotype code based on an identity of an antibiotic resistance gene determined from the first data, and a susceptibility code indicating an antibiotic to which the organism is non-susceptible. The method includes assigning a profile uniqueness identifier to the first subject, where the profile uniqueness identifier indicates a degree of similarity above a predetermined threshold between the first pattern and a known pattern associated with a classified subject. A first resistome profile is generated for the first subject based on the first pattern and the profile uniqueness identifier.

The present disclosure provides systems, apparatus, and methods for monitoring an infection state of a subject according to some embodiments. In one embodiment, a system for monitoring an infection state of a first subject includes at least one communication interface, at least one memory for storing processor executable instructions, and at least one processor, communicatively coupled to the at least one communication interface and the at least one memory. Upon execution of the processor-executable instructions, the at least one processor generates a first resistome profile for the first subject based on first data representative of at least one measure of antibiotic resistance of an organism from a first sample, generates a second resistome profile for the first subject based on second data representative of at least one measure of antibiotic resistance of an organism from a second sample, compares the first resistome profile to the second resistome profile, and determines a degree of difference above a threshold between the first resistome profile and the second resistome profile, wherein the degree of difference above the threshold between the first resistome profile and the second resistome profile indicates a change in the infection state of the first subject. In an embodiment, the at least one processor further determines and/or modifies a course of treatment for the first subject based on at least the change in the infection state of the first subject.

In one embodiment, a method includes generating a first resistome profile for the subject based on first data representative of a first sample derived from the subject, and generating a second resistome profile for the subject based on second data representative of a second sample derived from the subject. The resistome profiles may be generated using any method described herein. The first resistome profile is compared to the second resistome profile, and a difference between the first resistome profile and the second resistome profile is indicating a change in the infection state.

The present disclosure also provides systems, apparatus, and methods for determining an infection state of two or more subjects according to some embodiments. In one embodiment, a system for determining an infection state of at least one subject includes at least one communication interface, at least one memory for storing processor executable instructions, and at least one processor, communicatively coupled to the at least one communication interface and the at least one memory. Upon execution of the processor-executable instructions, the at least one processor generates a first resistome profile for a first subject based on first data representative of at least one measure of antibiotic resistance of an organism from a first sample, generates a second resistome profile for a second subject based on second data representative of at least one measure of antibiotic resistance of an organism from a second sample, compares the first resistome profile to the second resistome profile, and assigns at least one infection category to at least one of the first subject and the second subject based at least in part on the comparison of the first resistome profile to the second resistome profile, the at least one infection category indicating at least one infection state. In an embodiment, the at least one processor further determines and/or modifies a course of treatment for at least one of the first subject and the second subject based on the at least one infection category assigned to at least one of the first subject and the second subject.

In one embodiment, a method includes determining a first resistome profile for a first subject based on first data representative of at least one first measure of antibiotic resistance of a first organism, from a first biological sample obtained from the first subject, and determining a second resistome profile for a second subject based on second data representative of at least one second measure of antibiotic resistance of a second organism, from a second biological sample derived from the second subject. The resistome profiles may be generated using any method described herein. The first resistome profile is compared to the second resistome profile, at least one of the first subject and the second subject is assigned to an infection category based on the comparing. The infection category provides an indication of the infection state.

The present disclosure also provides systems, apparatus, and methods for identifying an infection outbreak at a facility according to some embodiments. In one embodiment, a system for monitoring risk of an infection outbreak at a facility includes at least one communication interface, at least one memory for storing processor executable instructions, and at least one processor, communicatively coupled to the at least one communication interface and the at least one memory. Upon execution of the processor-executable instructions, the at least one processor generates a first resistome profile for a first subject based on first data representative of at least one measure of antibiotic resistance of an organism from a first sample, compares the first resistome profile to a plurality of candidate resistome profiles, each candidate resistome profile of the plurality of candidate resistome profiles being associated with the facility and ranked according to a potential basis for indicating an infection outbreak, and determines a degree of similarity above a first threshold between the first resistome profile and each candidate resistome profile. If at least one candidate resistome profile has at least one degree of similarity above the first threshold with the first resistome profile, the at least one processor determines a degree of rank above a second threshold according to the potential basis for indicating an infection outbreak. If the at least one candidate resistome profile has at least one degree of rank above the second threshold, the at least one processor assigns to the facility a classification indicating risk of an infection outbreak.

In an embodiment, the plurality of candidate resistome profiles is stored in a computer database. A candidate resistome profile may include a phenotype code indicating a carbapenem-resistant Enterobacteriaceae is ranked above the second threshold according to a high potential basis for indicating an infection outbreak. The system may include a graphical display communicatively coupled to the at least one processor. Upon execution of the processor-executable instructions, the at least one processor may display an indication of the classification using a graphical representation. The graphical representation may include a quick response (QR) code, a tube graph, and/or an epidemiology star chart.

In one embodiment, a method includes determining a first resistome profile for a first subject based on first data representative of at least one measure of antibiotic resistance of a first organism, from a first biological sample obtained from the first subject. The resistome profile may be generated using any method described herein. The first resistome profile is compared to a plurality of candidate resistome profiles, each candidate resistome profile of the plurality of candidate resistome profiles being determined for a known subject associated with the facility. Each candidate resistome profile is ranked according to a potential basis for indicating an infection outbreak. The method includes identifying each candidate resistome profile of the plurality of candidate resistome profiles that has a degree of similarity above a predetermined threshold with the first resistome profile, and classifying the facility as being at risk of an infection outbreak if at least one of the candidate resistome profiles is ranked as potentially indicating an infection outbreak.

In one embodiment, a system includes at least one memory for storing processor executable instructions, and at least one processor, communicatively coupled to the at least one memory. Upon execution of the processor-executable instructions, the at least one processor performs any of the methods described herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
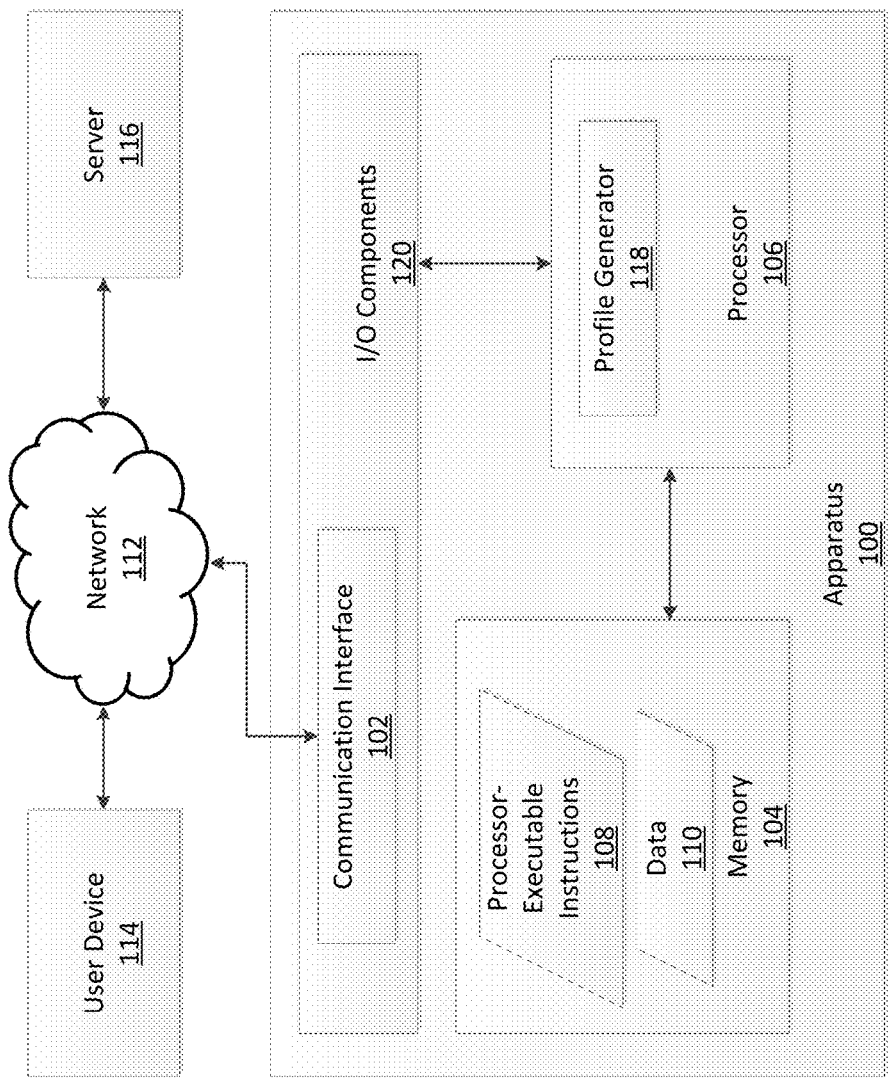
FIG. 1 illustrates an apparatus in accordance with some embodiments.

According to some embodiments, systems, apparatus, and methods disclosed herein provide a bioinformatics solution for diagnosing infected and colonized patients in a manner far exceeding conventional approaches to improve patient treatment, control pathogen transmission, manage health care infections, and track public health. These systems, methods, and/or apparatus may constitute a fully integrated set of analytical and reporting tools to facilitate infection control and infection state management for a single patient, a plurality of patients, or up to and including an entire patient population. These systems, apparatus, and methods may encompass or contribute to a comprehensive molecular diagnostic and bioinformatics platform to, for example, generate a resistome profile for a subject, monitor an infection state of one or more subjects, and/or identify a potential infection outbreak at a facility.

The systems, methods, and/or apparatus may facilitate identification of, for example, antibiotic resistant Gram-negative bacilli with superior throughput, sensitivity, and genotype resolution. Infected and/or colonized patients may be diagnosed in a manner that reduces pathogen transmission in healthcare settings. Meanwhile, the epidemiological progression of emerging antibiotic resistance patterns may be mapped on a global and local healthcare institute level. For example, pathogen information may be used to help guide antibiotic therapy and stewardship programs in acute care settings. The overall approach described herein also may be used in areas of infectious disease—including but not limited to tuberculosis, malaria, gonorrhea, Gram-positive organisms, fungi, and viruses—where multi-drug resistance is an issue. The systems, apparatus, and methods described herein may provide classification of infectious organisms that encompasses multiple variant organism types.

In some embodiments, antibiotic resistance genetic profiles may be combined with organism identification data and other diagnostic test results to provide unique organism/isolate profiles ("resistome profiles") that may be used to compare with, match, and/or differentiate from other resistome profiles from a plurality of subjects and environmental swabs for real-time outbreak and organism/isolate likeness information to help guide infection control activities. For example, useful information on antibiotic resistance and susceptibility information may be gained by testing isolates from infected patients who have had central line blood infections, ventilator associated pneumonia, urinary tract infections, or surgical site infections. In some embodiments, resistome profiles are generated using data from direct DNA tests, including, but not limited to, a multi-drug resistant organism gene detection system or any other DNA sequencing test on samples or culture isolates. Thus, antibiotic resistance information may be applied and developed further through sample testing and analysis processes to facilitate early and ready access to valuable information regarding organism species and antibiotic resistance that may be used to guide subject treatment and infection management according to some embodiments. In some embodiments, DNA sequence-based genomic data may be used for providing community profiling, pathogenicity prediction, strain attribution, or surveillance. In some embodiments, systems, apparatus, and methods facilitate combining the interpretation of sequence information, and phenotype information (as appropriate), with a similarity matching and numbering system.

Facility administrators, private industries, and public health agencies (including the U.S. Centers for Disease Control and Prevention (CDC) or the equivalent) may utilize systems, apparatus, and methods according to some embodiments for infectious disease management. Resistome profiles derived from colonized and/or infected subjects may be used to populate databases, and to guide infection management based on, for example, recommendations for isolation and modifications to disinfection procedures. An analysis engine (e.g., operating as a database engine) may be used to create and manage resistome profiles. The analysis engine also may be used to automatically check either individual facility databases or large hosted databases for matching patterns or profiles.

Unique, new matches to a particular database may be numbered on an ordered basis using a profile uniqueness identifier at the end of the resistome profile. The first number in the profile uniqueness identifier is the ordered individual match, and the second number in the profile uniqueness identifier is the ordered number of times there is a subject match in the database. Individual facilities may use this information to provide detailed diagnostic information, identify and track patients and individual isolates. Alternatively, a centralized lab may host a database and provide diagnostic results, for providing identification, matching, and value-add reporting services to clients. Results may also be generated in silico from third party data in computerized databases.

If there is a matching resistome profile for two or more subjects, a common infection may be occurring. Whether an individual subject being colonized with a matching resistome profile is important information for, among other things, infection management. If a subject becomes infected, rather than just colonized, the proper antibiotic for treating the individual subject, based on the information from the matching resistome profile, may be used until other antibiotic resistance and organism identification data is available. Using the analysis engine, clusters of subjects with common infections and prevalent resistome profiles may be identified and tracked over time and over geographic locations.

In some embodiments, common resistome profiles prevalent in an intensive care unit (ICU) or a long term care facility may be identified as a potential indicator of an outbreak among patients. In other embodiments, common resistome profiles prevalent in an livestock facility may be identified as a potential indicator of an outbreak among animals. In any context, systems, apparatus, and methods provided herein may be implemented to classify a population, such as a population associated with a facility. Based on a classification, agents of a facility, including, but not limited to, doctors or veterinarians, may be alerted to emerging infections (e.g., hospital acquired infections (HAIs)) and infection outbreaks as soon as common resistome profiles are associated with multiple subjects (e.g., S1:VIM:DP-N_MPN:27-2, as described further herein).

It should be appreciated that all combinations of these concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Definitions

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer. In some embodiments, to a only (optionally including elements other than B); in another embodiment, to B only (optionally including elements other than a); in yet another embodiment, to both a and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of a and B" (or, equivalently, "at least one of a or B," or, equivalently "at least one of a and/or B") may refer. In some embodiments, to at least one, optionally including more than one, a, with no B present (and optionally including elements other than B); in another embodiment, to at least one, optionally including more than one, B, with no a present (and optionally including elements other than a); in yet another embodiment, to at least one, optionally including more than one, a, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, the terms "about" and "approximately" are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "e.g." is used merely by way of example, without limitation intended, and should not be construed as referring only those items explicitly enumerated in the specification.

As used herein, the term "infection" is meant to include any infectious agent of bacterial origin. The bacterial infection may be the result of Gram-positive, Gram-negative bacteria or atypical bacteria.

As used herein, "Gram-positive bacteria" are bacteria that are stained dark blue by Gram staining. Gram-positive organisms are able to retain the crystal violet stain because of the high amount of peptidoglycan in the cell wall.

As used herein, "Gram-negative bacteria" are bacteria that do not retain the crystal violet dye in the Gram staining protocol.

As used herein, a "multi-drug resistant organism" is a microorganism (bacteria, viruses, fungi or parasites) that is resistant to distinct antimicrobial agents, first and foremost antibiotics, but also antifungal drugs, antiviral medications, and antiparasitic drugs.

Multi-drug resistant organisms may include, but are not limited to, organisms belonging to the genus *Acinetobacter, Citrobacter, Enterobacter, Enteroccus, Escherichia, Kiebsiella, Serratia* or Staphyloccus. Exemplary multi-drug resistant organisms include *Acinetobacter Baumannii* such as ATCC isolate #2894233-696-101-1, ATCC isolate #2894257-696-101-1 ATCC isolate #2894255-696-101-1, ATCC isolate #2894253-696-101-1, or ATCC #2894254-696-101-1; *Citrobacter freundii* such as ATCC isolate #33128, ATCC isolate #2894218-696-101-1, ATCC isolate #2894219-696-101-1, ATCC isolate #2894224-696-101-1, ATCC isolate #2894218-632-101-1, or ATCC isolate #2894218-659-101-1; *Enterobacter cloacae* such as ATCC isolate #22894251-659-101-1, ATCC isolate #22894264-659-101-1, ATCC isolate #22894246-659-101-1, ATCC isolate #22894243-659-101-1, or ATCC isolate #22894245-659-101-1; *Enteroccus facalis* such as ATCC isolate #22894228-659-101-1 ATCC isolate #22894222-659-101-1, ATCC isolate #22894221-659-101-1, ATCC isolate #22894225-659-101-1, or ATCC isolate #22894245-659-101-1; *Enteroccus faecium* such as ATCC isolate #51858, ATCC isolate #35667, ATCC isolate #2954833_2694008 ATCC isolate #2954833_2692765, or ATCC isolate #2954836_2694361; *Escherichia coli* such as ATCC isolate CGUC 11332, CGUC 11350, CGUC 11371, CGUC 11378, or CGUC 11393; Kiebsiella pneumonia such as ATTC isolate #27736, ATTC isolate #29011, ATTC isolate #20013, ATTC isolate #33495, or ATTC isolate #35657; *Serratia marcescens* such as ATCC isolate #43862, ATCC isolate #2338870, ATCC isolate #2426026, ATCC isolate #SIID 2895511, or ATCC isolate #SIID 2895538; or Staphyloccus *aureus* such as ATCC isolate #JHH 02, ATCC isolate #JHH 02, ATCC isolate #JHH 03, ATCC isolate #JHH 04, ATCC isolate #JHH 05, or ATCC isolate #JHH 06.

As used herein, "CRE" refers to carbapenem-resistant Enterobacteriaceae.

As used herein, "ESBL" refers to extended spectrum beta lactamase.

As used herein, a "method of treating" includes a method of managing, and when used in connection with the biological organism or infection, may include the amelioration, elimination, reduction, prevention, and/or other relief from a detrimental effect of a biological organism. Detrimental effects may include a mycobacterial infection, symptoms characterizing and/or effects associated with tuberculosis in the subject, or a combination thereof.

As used herein, "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As used herein, "DNA segment" refers to a DNA molecule that has been isolated free of total genomic DNA of a particular species. Therefore, a DNA segment obtained from a biological sample using one of the compositions described herein refers to one or more DNA segments that have been isolated away from, or purified free from, total genomic DNA of the particular species from which they are obtained, and also in the case of pathogens, optionally isolated away from, or purified free from total mammalian (preferably human) genomic DNA of the infected individual. Included within the term "DNA segment," are DNA segments and smaller fragments of such segments, as well as recombinant vectors, including, for example, plasmids, cosmids, phage, viruses, and the like.

As used herein, "RNA segment" refers to an RNA molecule that has been isolated free of total cellular RNA of a particular species. Therefore, RNA segments obtained from a biological sample using one of the compositions disclosed herein, refers to one or more RNA segments (either of native or synthetic origin) that have been isolated away from, or purified free from, other RNAs. Included within the term "RNA segment," are RNA segments and smaller fragments of such segments.

As used herein, the terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of ordinary skill) or by visual inspection.

As used herein, the phrase "substantially identical," in the context of two nucleic acids refers to two or more sequences or subsequences that have at least about 90%, preferably 91%, most preferably about 92%, 93%, 94%, 95%, 96%, 97%, 98%, 98.5%, 99%, 99.1%, 99.2%, 99.3%, 99.4%, 99.5%, 99.6%, 99.7%, 99.8%, 99.9% or more nucleotide residue identity, when compared and aligned for maximum correspondence, as measured using a sequence comparison algorithm or by visual inspection. Such "substantially identical" sequences are typically considered "homologous," without reference to actual ancestry.

As used herein, "sample" includes anything containing or presumed to contain a substance of interest. It thus may be a composition of matter containing nucleic acid, protein, or another biomolecule of interest. The term "sample" may thus encompass a solution, cell, tissue, or population of one or more of the same that includes a population of nucleic acids (genomic DNA, cDNA, RNA, protein, other cellular molecules, etc.). The terms "nucleic acid source," "sample," and "specimen" are used interchangeably herein in a broad sense, and are intended to encompass a variety of biological sources that contain nucleic acids, protein, one or more other biomolecules of interest, or any combination thereof. Exemplary biological samples include, but are not limited to, whole blood, plasma, serum, sputum, urine, stool, white blood cells, red blood cells, buffy coat, swabs (including, without limitation, buccal swabs, throat swabs, vaginal swabs, urethral swabs, cervical swabs, rectal swabs, lesion swabs, abscess swabs, nasopharyngeal swabs, and the like), urine, stool, sputum, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchial or pulmonary lavage, lung aspirates, and organs and tissues, including but not limited to, liver, spleen, kidney, lung, intestine, brain, heart, muscle, pancreas, and the like, and any combination thereof. Tissue culture cells, including explanted material, primary cells, secondary cell lines, and the like, as well as lysates, homogenates, extracts, or materials obtained from any cells, are also within the meaning of the term "biological sample," as used herein. The ordinary-skilled artisan will also appreciate that lysates, extracts, or materials obtained from any of the above exemplary biological samples are also within the scope of the invention.

As used herein, "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, "patient" (also interchangeably referred to as "host" or "subject") refers to any host that may serve as a source of one or more of the biological samples or specimens as discussed herein. In certain aspects, the donor will be a vertebrate animal, which is intended to denote any animal species (and preferably, a mammalian species such as a human being). In certain embodiments, a "patient" refers to any animal host, including but not limited to, human and non-human primates, avians, reptiles, amphibians, bovines, canines, caprines, cavities, corvines, epines, equines, felines, hircines, lapines, leporines, lupines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

As used herein, the term "substantially free" or "essentially free," as used herein, typically means that a composition contains less than about 10 weight percent, preferably less than about 5 weight percent, and more preferably less than about 1 weight percent of a compound. In a preferred embodiment, these terms refer to less than about 0.5 weight percent, more preferably less than about 0.1 weight percent or even less than about 0.01 weight percent. The terms encompass a composition being entirely free of a compound or other stated property, as well. With respect to degradation or deterioration, the term "substantial" may also refer to the above-noted weight percentages, such that preventing substantial degradation would refer to less than about 15 weight percent, less than about 10 weight percent, preferably less than about 5 weight percent, etc., being lost to degradation. In other embodiments, these terms refer to mere percentages rather than weight percentages, such as with respect to the term "substantially non-pathogenic" where the term "substantially" refers to leaving less than about 10 percent, less than about 5 percent, etc., of the pathogenic activity.

As used herein, "heterologous" is defined in relation to a predetermined referenced nucleic acid sequence. For example, with respect to a structural gene sequence, a heterologous promoter is defined as a promoter that does not naturally occur adjacent to the referenced structural gene, but which is positioned by the hand of man in one or more laboratory manipulations that are routinely employed by those of ordinary skill in the molecular biological arts. Likewise, a heterologous gene or nucleic acid segment is defined as a gene or nucleic acid segment that does not naturally occur adjacent to the referenced sequence, promoter and/or enhancer element(s), etc.

As used herein, the term "healthy" refers to a state of an individual who is not at high risk of being infected with a multi-drug resistant organism.

As used herein, "homology" refers to a degree of complementarity between two or more polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity may be determined by analyzing two or more sequences using algorithms and computer programs known in the art. Such methods may be used to assess whether a given sequence is identical or homologous to another selected sequence.

As used herein, "homologous" means, when referring to polynucleotides, sequences that have the same essential nucleotide sequence, despite arising from different origins. Typically, homologous nucleic acid sequences are derived from closely related genes or organisms possessing one or more substantially similar genomic sequences. By contrast, an "analogous" polynucleotide is one that shares the same function with a polynucleotide from a different species or organism, but may have a significantly different primary nucleotide sequence that encodes one or more proteins or polypeptides that accomplish similar functions or possess similar biological activity. Analogous polynucleotides may often be derived from two or more organisms that are not closely related (e.g., either genetically or phylogenetically).

As used herein, the terms "identical" or percent "identity", in the context of two or more nucleic acid or polynucleotide sequences, refer to two or more sequences or subsequences that are the same or have a specified percentage of nucleotides that are the same, when compared and aligned for maximum correspondence over a comparison window, as measured using a sequence comparison algorithm or by manual alignment and visual inspection.

As used herein, a "primer" or "primer sequence" may include any nucleic acid sequence or segment that selectively hybridizes to a complementary template nucleic acid strand ("target sequence") and functions as an initiation point for the addition of nucleotides to replicate the template strand. Primer sequences of the present disclosure may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

As used herein, a "target sequence" or "target nucleotide sequence" as used herein includes any nucleotide sequence to which one of the disclosed primer sequences hybridizes under conditions that allow an enzyme having polymerase activity to elongate the primer sequence, and thereby replicate the complementary strand.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" may be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As used herein, "protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of about 2 to about 20 amino acid residues in length, oligopeptides of about 10 to about 100 amino acid residues in length, and polypeptides of about 100 to about 5,000 or more amino acid residues in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5' to 3' order of nucleotides.

As used herein, the term "substantially homologous" encompasses two or more biomolecular sequences that are significantly similar to each other at the primary nucleotide sequence level. For example, in the context of two or more nucleic acid sequences, "substantially homologous" may refer to at least about 75%, preferably at least about 80%, and more preferably at least about 85%, or at least about 90% identity, and even more preferably at least about 95%, more preferably at least about 97% identical, more preferably at least about 98% identical, more preferably at least about 99% identical, and even more preferably still, entirely identical (i.e., 100% or "invariant").

Likewise, as used herein, the term "substantially identical" encompasses two or more biomolecular sequences (and in particular polynucleotide sequences) that exhibit a high degree of identity to each other at the nucleotide level. For example, in the context of two or more nucleic acid sequences, "substantially identical" may refer to sequences that at least about 80%, and more preferably at least about 85% or at least about 90% identical to each other, and even more preferably at least about 95%, more preferably at least about 97% identical, more preferably at least about 98% identical, more preferably at least about 99% identical, and even more preferably still, entirely identical (i.e., 100% identical or "non-degenerate").

As used herein, the term "recombinant" indicates that the material (e.g., a polynucleotide or a polypeptide) has been artificially or synthetically (non-naturally) altered by human intervention. The alteration may be performed on the material within or removed from, its natural environment or state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant influenza virus, is produced by the expression of a recombinant nucleic acid.

As used herein, the term "operably linked" refers to a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and in reading frame. Since enhancers generally function when separated from the promoter by several kilobases and intronic sequences may be of variable lengths; however, some polynucleotide elements may be operably linked but not contiguous.

As used herein, the phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, "link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

As used herein, "plasmid" refers to a genetic construct that is composed of genetic material (i.e., nucleic acids). Typically, a plasmid contains an origin of replication that is functional in bacterial host cells, e.g., *Escherichia coli*, and selectable markers for detecting bacterial host cells including the plasmid. Plasmids of the present invention may include one or more genetic elements as described herein arranged such that an inserted coding sequence may be transcribed and translated in a suitable expression cells. In addition, the plasmid may include one or more nucleic acid segments, genes, promoters, enhancers, activators, multiple cloning regions, or any combination thereof, including segments that are obtained from or derived from one or more natural and/or artificial sources.

As used herein, "resistome" refers to a collection of antibiotic resistance genes and/or their precursors in both pathogenic and non-pathogenic bacteria, which may be comprised of antibiotic resistance genes found on antibiotic producers, such as microorganisms in soil-dwelling bacteria and fungi that naturally produce antibiotics which have their own protection mechanisms to avoid the adverse effects of the antibiotics on themselves, and cryptic resistance genes embedded in the bacterial chromosome, and precursor genes which may not confer antibiotic resistance but may encode proteins that confer to some kind of basal level activity against the antibiotic molecule or have affinity to the molecule, and antibiotic resistance genes associated with bacterial biochemical, enzyme, and molecular regulatory pathways which may confer antibiotic resistance including, for example, genes affiliated with efflux pumps and cell wall porins.

Multi-Drug Resistant Organisms (MDROs)

According to some embodiments, the systems, apparatus, and methods disclosed herein provide a bioinformatics solution for rapidly detecting, tracking, and controlling multi-drug resistant organisms (MDROs) in a single subject or a population of subjects at risk for infection by or colonized or infected with MDROs. Detection of MDRO-colonized or infected subjects may aid in individual infection state management (e.g., the selection of appropriate antibiotic therapy) and larger scale infection control (e.g., containment).

For example, the systems, apparatus, and methods disclosed herein may be used to detect beta-lactamase genes found in beta-lactam antibiotic resistant Gram-negative bacteria and vancomycin-resistant genes found in vancomycin-resistant Gram-positive bacteria. More specifically, the systems, apparatus, and methods disclosed herein may be used to detect genes, including, but not limited to, *Klebsiella pneumoniae* carbapenemase (KPC), New Delhi Metallo-beta-lactamase (NDM), Verona integron-encoded metallo-beta-lactamase (VIM), IMP-type carbapenemase (IMP), and OXA beta-lactamase (OXA) genes found in carbapenem-resistant Gram-negative bacteria; CTX-M beta-lactamase (CTX-M) genes found in extended spectrum resistant Gram-negative bacteria; and Van-A found in vancomycin-resistant enterococci (VRE).

Genes that confer multi-drug resistance to organisms are referred to herein as MDRO-associated genes and may encompass one or more of KPC, NDM, VIM, IMP, OXA, CTX-M, and Van-A, including all family members. For example, reference to KPC includes KPC-2 and KPC-16. Further description of these MDRO-associated genes is provided herein.

KPC (*K. pneumoniae* Carbapenemase) (Class A)

A few class A enzymes, most noted the plasmid-mediated KPC enzymes, are effective carbapenemases as well. Ten variants, KPC-2 through KPC-11 are known, and they are distinguished by one or two amino acid substitutions (KPC-1 was re-sequenced in 2008 and found to be 100% homologous to published sequences of KPC-2). KPC-1 was found in North Carolina, KPC-2 in Maryland, and KPC-3 in New York. They have only 45% homology with SME and NMC/IMI enzymes and, unlike them, may be encoded by self-transmissible plasmids.

The class A *Klebsiella pneumoniae* carbapenemase (KPC) is currently the most common carbapenemase, which was first detected in North Carolina, US, in 1996 and has since spread worldwide. A later publication indicated that Enterobacteriaceae that produce KPC were becoming common in the United States.

NDM (New Delhi Metallo-Beta-Lactamase) (Class B)

Originally described from New Delhi in 2009, this gene is now widespread in *Escherichia coli* and *Klebsiella pneumoniae* from India and Pakistan. As of mid-2010, NDM carrying bacteria have been introduced to other countries (including the United States and the United Kingdom of Great Britain), most probably due to the large number of tourists traveling the globe, who may have picked up the strain from the environment, as strains containing the NDM gene have been found in environmental samples in India Ten gene subtypes have been reported for NDM: NDM-1 to NDM-10.

VIM (Verona Integron-Encoded Metallo-Beta-Lactamase) (Class B)

A second growing family of carbapenemases, the VIM family now includes forty members, which have a wide geographic distribution in Europe, South America, and East Asia and have been found in the United States. VIM-1 was discovered in *P. aeruginosa* in Italy in 1996; since then, VIM-2, which is now the predominant variant has been found repeatedly in Europe and East Asia; VIM-3 and VIM-4 are minor variants of VIM-2 and VIM-1, respectively. Forty gene subtypes have been reported for VIM: VIM-1 to VIM-40. VIM enzymes occur mostly in *P. aeruginosa*, and also in *P. putida* and, very rarely, in Enterobacteriaceae.

Amino acid sequence diversity is up to 10% in the VIM family, 15% in the IMP family, and 70% between VIM and IMP. Enzymes of both the families, nevertheless, are similar. Both are integron-associated, sometimes within plasmids. Both hydrolyse all beta-lactams except monobactams, and evade all beta-lactam inhibitors.

IMP-Type Carbapenemases (Metallo-Beta-Lactamases) (Class B)

Plasmid-mediated IMP-type carbapenemases, 48 varieties (IMP 1-IMP48) of which are currently known, became established in Japan in the 1990s both in enteric Gram-negative organisms and in *Pseudomonas* and *Acinetobacter* species. IMP enzymes spread slowly to other countries in East Asia, were reported from Europe in 1997, and have been found in Canada and Brazil.

OXA Beta-Lactamases (Class D)

OXA beta-lactamases were long recognized as a less common but also plasmid-mediated beta-lactamase variety that could hydrolyze oxacillin and related anti-staphylococcal penicillins. These beta-lactamases differ from the TEM and SHV enzymes in that they belong to molecular class D and functional group 2d. The OXA-type beta-lactamases confer resistance to ampicillin and cephalothin and are characterized by their high hydrolytic activity against oxacillin and cloxacillin and the fact that they are poorly inhibited by clavulanic acid. Amino acid substitutions in OXA enzymes may also give the ESBL phenotype. While most ESBLs have been found in *E. coli, K. pneumoniae*, and other Enterobacteriaceae, the OXA-type ESBLs have been found in *P. aeruginosa* and *Acinetobacter buamannii*. OXA-type ESBLs have been found mainly in *Pseudomonas aeruginosa* isolates from Turkey and France.

The OXA beta-lactamase family was originally created as a phenotypic rather than a genotypic group for a few beta-lactamases that had a specific hydrolysis profile. Therefore, there is as little as 20% sequence homology among some of the members of this family. However, recent additions to this family show some degree of homology to one or more of the existing members of the OXA beta-lactamase family. Some confer resistance predominantly to ceftazidime, but OXA-17 confers greater resistance to cefotaxime and cefepime than it does resistance to ceftazidime.

CTX-M Beta-Lactamases (Class A)

These enzymes were named for their greater activity against cefotaxime than other oxyimino-beta-lactam substrates (e.g., ceftazidime, ceftriaxone, or cefepime). Rather than arising by mutation, they represent examples of plasmid acquisition of beta-lactamase genes normally found on the chromosome of *Kluyvera* species, a group of rarely pathogenic commensal organisms. These enzymes are not very closely related to TEM or SHV beta-lactamases in that they show only approximately 40% identity with these two commonly isolated beta-lactamases. More than eighty CTX-M enzymes are currently known.

Van-A

Six different types of vancomycin resistance are shown by *Enterococcus*: Van-A, Van-B, Van-C, Van-D, Van-E and Van-F. Of these, only Van-A, Van-B, and Van-C have been seen in general clinical practice, so far. The significance is that Van-A is resistant to both vancomycin and teicoplanin. The mechanism of resistance to vancomycin found in *enterococcus* involves the alteration to the terminal amino acid residues of the NAM/NAG-peptide subunits, under normal conditions, D-alanyl-D-alanine, to which vancomycin binds. The D-alanyl-D-lactate variation results in the loss of one hydrogen-bonding interaction (four, as opposed to five for D-alanyl-D-alanine) being possible between vancomycin and the peptide. This loss of just one point of interaction results in a 1000-fold decrease in affinity. The D-alanyl-D-serine variation causes a six-fold loss of affinity between vancomycin and the peptide, likely due to steric hindrance.

Resistome Profiles

According to some embodiments, dynamic naming and diagnostic systems, apparatus, and methods are implemented to identifying, diagnose, and manage subjects with complex drug resistant infections. FIG. 1 illustrates an apparatus 100 for generating resistome profiles in accordance with some embodiments. For example, apparatus 100 may be used to implement the methods described herein. The apparatus 100 includes at least one communication interface 102, at least one memory 104, and at least one processor 106, which is communicatively coupled to the at least one communication interface 102 and the at least one memory 104.

The at least one memory 104 may be configured to store processor-executable instructions 108 and/or data 110. For example, data 110 may include raw sample data and/or processed data, such as data representative of at least one measure of antibiotic resistance of an organism. Data also may be stored on and/or accessed from an external computing device over at least one network 112 via the at least one communication interface 102. The external computing device, such as a user device 114 and/or a server 116 (e.g., cloud storage). Non-limiting examples of an external computing device include a smartphone, a Personal Digital assistant (PDA), a tablet computer, a laptop, a slate computer, an electronic reader (e-reader), or any other suitable portable or fixed electronic device.

According to some embodiments, the at least one processor 106 executes processor-executable instructions 108 to control the at least one communication interface 102 to communicate over at least one network with an external computing device 114, 116 and/or control the at least one memory 104 to store and/or retrieve data. In some embodiments, the at least one processor 106 includes a profile generator 118, by which the at least one processor 106 executes processor-executable instructions 108 stored in the at least one memory 104 to receive and analyze data representative of a measure of antibiotic resistance of an organism in a sample obtained from a subject, identify the organism, determine at least one of an antibiotic susceptibility phenotype, an antibiotic resistance gene, and an antibiotic to which the organism is non-susceptible, and thereby generate at least one actionable resistome profile for the subject. A resistome profile may be assigned to one or more bacterial isolates from a sample. In some embodiments, the at least one processor 106 may be configured to execute processor-executable instructions 108 stored in the at least one memory 104 to monitor an infection state of one or more subjects and classify a population (e.g., facility) as to potential outbreak risk, as described further herein.

Figure 2:
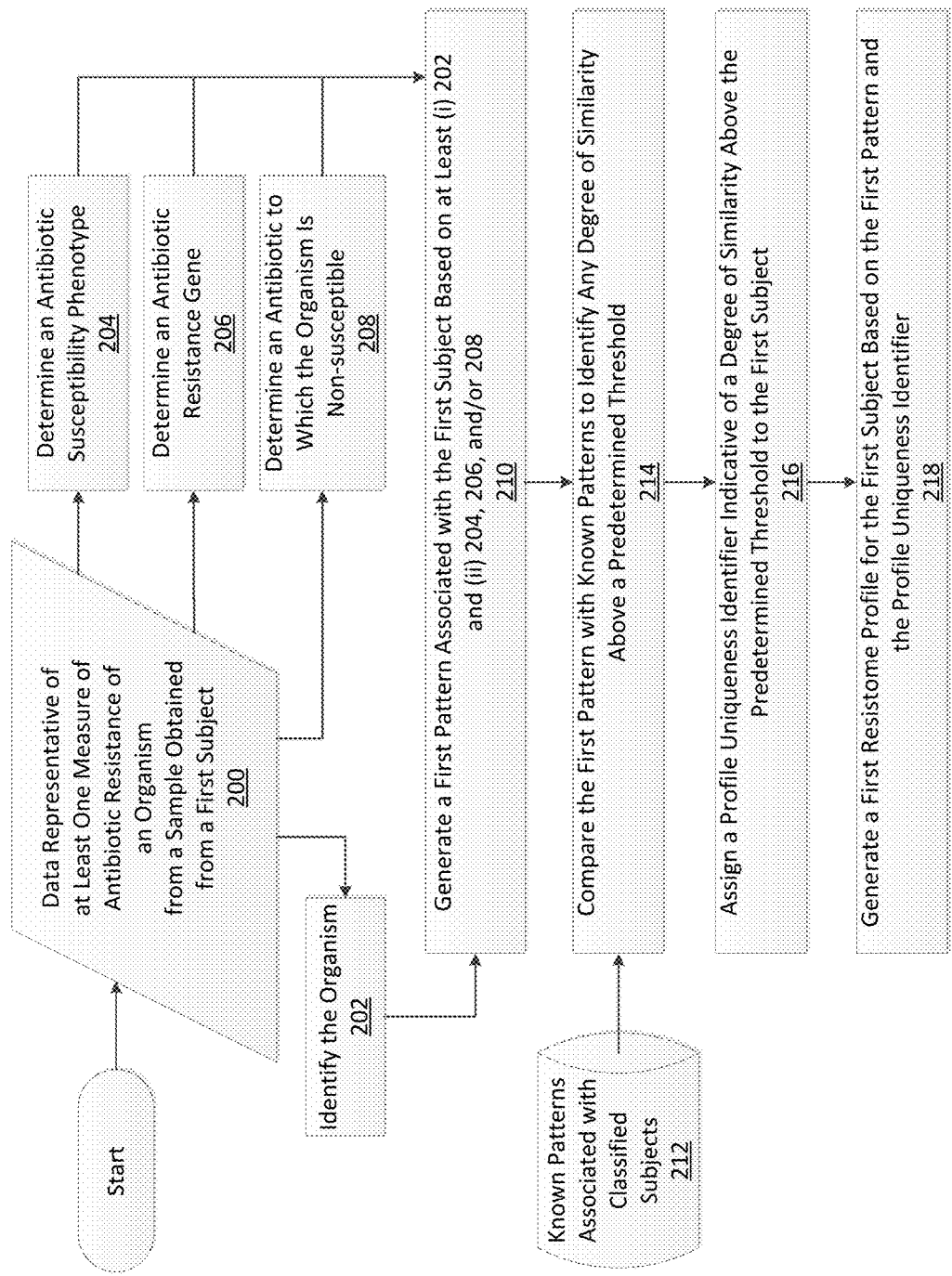
FIG. 2 is a flowchart illustrating a method of generating a resistome profile in accordance with some embodiments.

FIG. 2 is a flowchart illustrating a method for generating a resistome profile for a subject, based on a sample obtained from a subject according to some embodiments. In step 200, data representative of at least one measure of antibiotic resistance of an organism in a sample from a subject is obtained. The sample may be any biological sample obtained from the subject, including, but not limited to, at least one of an anal swab, a rectal swab, a skin swab, nasal swab, wound swab, stool, blood, plasma, serum, urine, sputum, respiratory lavage, and a cerebrospinal fluid.

Data collected from analysis of the sample may be any type of biological or diagnostic data, including, but not limited to, data indicating at least one of a type or types of genes, a gene sequence or sequences, a gene family or families, a DNA sequence or sequences, one or more single-nucleotide polymorphisms (SNPs), a type or types of nucleic acids, a type or types of proteins, and protein expression. Data collected from analysis of a sample may include data representative of at least one of a DNA probe assay, a microbial identification test, and an antibiotic susceptibility test performed on a bacterial isolate from the sample. Alternatively or in addition, data collected from analysis of the sample may include data representative of at least one antibiotic resistance test performed on a bacterial isolate from the sample.

In some embodiments, DNA sequencing is used to identify organisms, indicate their genotype, genetically predict their antimicrobial resistance, or match organisms infecting or colonizing patients, using whole genome or targeted genome analysis. Where this detailed DNA sequence information is available on a timely or cost effective basis, phenotype information describing actual antibiotic susceptibility may be used as described herein.

In some embodiments, data from an MDRO gene detection system (e.g., but not limited to, the ACUITAS™ MDRO Gene Test System (available from OpGen, Inc., Gaithersburg, Md.)) is combined with phenotypically derived isolate identification and antibiotic resistance information. For example, the ACUITAS™ MDRO Gene Test is a first generation multiplex assay that provides information such as ESBL CTX type in groups (A, B, C). High resolution naming at the type level, for instance C9, C15, etc., or even higher resolution genotyping information also may be used.

In some embodiments, data representative of at least one measure of antibiotic resistance of an organism in a sample obtained from the subject may also include sample information, including, but not limited to, high resolution mass spectra for mass spectrometry data analysis to potentially identify the species or otherwise differentiate individual isolates. For example, a sample may be measured using matrix-assisted laser desorption ionization (MALDI) mass spectrometry, a soft ionization technique that allows analysis of biomolecules, which would otherwise tend to be fragile and fragment when ionized by more conventional ionization methods. In particular, the sample may be measured using a time-of-flight (TOF) mass spectrometer, such as the 4800 MALDI TOF/TOF™ Analyzer (available from Applied Biosystems®/MDS SCIEX, Grand Island, N.Y.) that doubles the ion flight path and increases the resolution. Mass spectrometry measurements may be used to identify isolate organisms from culture specimens using molecular weight profiles or to determine SNPs.

Data collected from analysis of a sample also may include data associated with an organism identified in the sample, including, but not limited to, at least one of a genome sequence of the identified organism, a minimum inhibitory concentration for an antibiotic, and in silico data from a reference organism involved in an outbreak.

In some embodiments, metadata associated with at least one of the subject and the sample is collected (with necessary consent of the subject as applicable), including, but not limited to, at least one of identification information (e.g., a patient identifier), demographic information, historical data (e.g., patient medical history), organization information (e.g., an agency or a diagnosis and/or treatment facility), phenotype, collection parameters (e.g., time, kit, media, etc.), and any other pertinent information associated with the subject and/or the sample. A diagnosis and/or treatment facility may be, but is not limited to, at least one of a hospital, a clinic, a health center, a dental office, a medical office, another private medical practitioner, a non-governmental agency facility, and a gerontology agency. An agency may include, but is not limited to, at least one of an insurance agency, a government agency, a non-government agency, and a gerontology agency.

In step 202 of FIG. 2, at least one organism in the sample is identified from the data representative of at least one measure of antibiotic resistance of an organism in the sample. An isolate organism may be identified in a sample using molecular weight profiles and mass spectrometry measurements (e.g., MALDI TOF).

In step 204 of FIG. 2, an antibiotic susceptibility phenotype may be determined from the data representative of at least one measure of antibiotic resistance of an organism in the sample.

In step 206 of FIG. 2, an antibiotic resistance gene may be determined from the data representative of at least one measure of antibiotic resistance of an organism in the sample.

In step 208 of FIG. 2, an antibiotic to which the organism is non-susceptible may be determined from the data representative of at least one measure of antibiotic resistance of an organism in the sample.

In step 210 of FIG. 2, a first pattern associated with the first subject is generated based on the identified organism and at least one of the determined antibiotic susceptibility phenotype, the determined antibiotic resistance gene, and the determined antibiotic to which the organism is non-susceptible. The first pattern may include:
an organism identification code to indicate the identified organism; and
at least one of:
a phenotype code, to indicate any antibiotic susceptibility phenotype as determined from the data representative of at least one measure of antibiotic resistance of an organism in the sample;
a genotype code, to indicate any antibiotic resistance gene as determined from the data representative of at least one measure of antibiotic resistance of an organism in the sample; and
a susceptibility code, to indicate any antibiotic to which the organism is non-susceptible as determined from the data representative of at least one measure of antibiotic resistance of an organism in the sample.

According to some embodiments, the first pattern may include a plurality of genotype codes, where each genotype code indicates the identity of a different antibiotic resistance gene associated with the identified organism.

According to some embodiments, a plurality of known patterns are stored in one or more databases, for example, in memory 104 of an apparatus for generating resistome profiles. Alternatively or in addition, patterns may be stored on an external computing device (e.g., in the cloud). Each known pattern may be associated with a classified subject. The classified subject may be a colonized or infected patient. According to some embodiments, colonized patients test positive for at least one drug-resistant organism, and infected patients have at least one of a central line blood infection, ventilator associated pneumonia, a urinary tract infection, and a surgical site infection. In some embodiments, the known patterns have been determined based on measurement data of at least one of antibiotic resistance and susceptibility performed on isolates from samples from the classified subjects.

Known patterns associated with classified subjects may be stored, for example, in a database of known patterns 212. In step 214 of FIG. 2, the first pattern is compared with the database of known patterns 212 to identify a degree of similarity, if any, between the first pattern and one or more of the known patterns. A similarity metric may be applied to compare the first pattern to a plurality of known patterns from previously classified subjects.

In some embodiments, a threshold of similarity between the first pattern and a known pattern is predetermined or determined. If a degree of similarity between the first pattern and any of the known patterns exceeds that threshold, as in step 216 of FIG. 2, a profile uniqueness identifier is assigned to the subject. The profile uniqueness identifier indicates the degree of similarity above the threshold between the first pattern and at least one known pattern associated with a classified subject.

A profile uniqueness identifier may be expressed using two or more identifier codes. One identifier code may be used to indicate a uniqueness of the first pattern compared to known patterns in the database 212, and another identifier code may be used to indicate how many profiles in the database share a sufficiently similar pattern (i.e., have a degree of similarity above the threshold). For example, a profile uniqueness identifier may include a sequential uniqueness code determined based on the degree of similarity above a threshold between the first pattern and at least one of the known patterns and a repetition index to indicate an increase in a number of known patterns that are sufficiently similar to the first pattern.

A profile uniqueness identifier may be determined based on additional information beyond that included in the known patterns or in resistome profiles generated based at least in part on the known patterns. Additional information may include nearest neighbor information. For example, when genome sequence data is available, a resistome profile may include information indicating a number of nucleotide differences from nearest neighbors, including, but not limited to, one or more locations of these differences in the nucleotide sequences. In fact, a nearest neighbor indicator may be included as a component of a profile uniqueness identifier and/or as a separate classification parameter of a resistome profile.

In step 218 of FIG. 2, a first resistome profile is generated for the subject based on the first pattern and the associated profile uniqueness identifier according to some embodiments. A resistome profile may be stored or output via a network or displayed to a user as a code notation. For example, a resistome profile may be stored, transmitted, and/or displayed as a character string representation (e.g., K1:CRE:KPC_O1 . . . ) or a user-specified notation (e.g., using a lookup table), as described further herein. In some embodiments, a resistome profile is displayed using a graphical representation, including, but not limited to, various shapes, colors, and symbols, a two-dimensional code (e.g., a QR code), a tube graph, and an epidemiology star chart.

A resistome profile may be generated with a pattern generator and analyzer, implemented, for example, as a database engine. The pattern generator and analyzer may determine pattern components from analysis of subject samples, generate patterns, apply similarity metrics, determine resistome profile components from analysis of patterns and subject sample metadata, and/or generate resistome profiles using rules based on the methods described herein. A resistome profiles may be constructed using a set of rules according to the principles described herein. The algorithms described herein, and associated systems, apparatus, and methods for implementing the rules are not limited to the examples herein, and may be altered or user-defined for greater flexibility and to support future expansion and changes in antibiotic resistomes and available antibiotic treatments.

Pattern Coding

According to some embodiments, a pattern associated with a subject sample is generated based on the identified organism and at least one of the determined antibiotic susceptibility phenotype, the determined antibiotic resistance gene, and the determined antibiotic to which the organism is non-susceptible. The pattern components may be defined by an organism identification code, phenotype code, genotype code, and/or susceptibility code, as described herein, or any other appropriate abbreviations or other representations beyond those described herein.

In some embodiments, the pattern includes an organism identification code to indicate an organism (i.e., organism species) identified in the subject sample. For example, the following may be used as the organism identification code for the organism indicated based on testing results for the measurement data: E for *Escherichia*, K for *Klebsiella*, A for *Acinetobacter*, P for *Pseudomonas*, etc. Other non-limiting examples of organism identification codes are shown below in TABLE 1:

TABLE 1

| Organism | Organism Full Name | Organism ID Code |
|---|---|---|
| A. baumannii | Acinetobacter baumannii | A1 |
| C. amalonaticus | Citrobacter amalonaticus | C4 |
| C. freundii | Citrobacter freundii | C1 |
| C. koseri | Citrobacter koseri | C3 |
| C. difficile | Clostridium difficile | C2 |
| E. aerogenes | Enterobacter aerogenes | E8 |
| E. cloacae | Enterobacter cloacae | E2 |
| E. cloacae complex | Enterobacter cloacae complex | E10 |
| E. gergoviae | Enterobacter gergoviae | E9 |
| E. avium | Enterococcus avium | E4 |
| E. canintestini | Enterococcus canintestini | E6 |
| E. faecalis | Enterococcus faecalis | E7 |
| E. faecium | Enterococcus faecium | E3 |
| E. raffinosus | Enterococcus raffinosus | E5 |
| E. coli | Escherichia coli | E1 |
| K. oxytoca | Klebsiella oxytoca | K3 |
| K. pneumoniae | Klebsiella pneumoniae | K2 |
| K. pneumoniae ssp ozaenae | Klebsiella pneumoniae ssp ozaenae | K4 |
| K. pneumoniae ssp pneumoniae | Klebsiella pneumoniae ssp pneumoniae | K1 |
| P. mirabilis | Proteus mirabilis | P3 |
| P. rettgeri | Providencia rettgeri | P4 |
| P. stuartii | Providencia stuartii | P2 |
| P. aeruginosa | Pseudomonas aeruginosa | P1 |
| S. enterica ser. Typhimurium | Salmonella enterica ser. Typhimurium | S3 |
| S. marcescens | Serratia marcescens | S1 |
| S. aureus | Staphylococcus aureus | S2 |
| S. maltophilia | Stenotrophomonas maltophilia | S4 |

In some embodiments, the pattern includes a phenotype code to indicate any corresponding antibiotic susceptibility phenotype of the identified organism, as determined from the subject sample. Some non-limiting examples of phenotype codes are shown below in TABLE 2:

TABLE 2

| Antibiotic Bacterial Phenotype | Phenotype Code |
|---|---|
| Cephalosporin-resistant (3rd or 4th generation) Gram-negative bacillus | CephR-GNB |
| Carbapenem-resistant Enterobacteriaceae | CRE |
| Carbapenem-resistant Gram-negative bacillus | CR-GNB |
| Extended-spectrum beta-lactamase | ESBL |
| Susceptible Gram-negative bacillus | S-GNB |
| Vancomycin-resistant enterococcus | VRE |
| Vancomycin-susceptible enterococcus | VSE |

In some embodiments, the pattern includes a genotype code to indicate any antibiotic resistance gene or corresponding family of genes as determined from the subject sample. The first pattern may include a plurality of genotype codes, where each genotype code indicates the identity of a different antibiotic resistance gene or corresponding gene family associated with the identified organism as determined from the subject sample. Some non-limiting examples of genotype codes are shown below in TABLE 3:

TABLE 3

| Antibiotic Resistance Gene Family | Genotype Code |
|---|---|
| C. difficile binary | BIN |
| CTX-M-1 | CTX1 or C1 |
| CTX-M-2 | CTX2 or C2 |
| CTX-M-25 | CTX25 or C25 |
| CTX-M-8 | CTX8 or C8 |
| CTX-M-9 | CTX9 or C9 |
| IMP | IMP |
| KPC | KPC |
| C. difficile NAP1 | NAP1 |
| NDM | NDM |
| OXA-23 | O23 |
| OXA-24 | O24 |
| OXA-48 | O48 |
| OXA-51 | O51 |
| OXA-58 | O58 |
| SHV(aa238) | S238 |
| SHV(aa240) | S240 |
| TEM(aa104) | T104 |
| TEM(aa164) | T164 |
| TEM(aa238) | T238 |
| TEM(aa240) | T240 |
| C. difficile tcdB | TXB |
| C. difficile tcdC | TXC |
| VanA | VANA |
| VIM(A/B) | VIM |
| VIM(C) | VIMC |

In some embodiments, the pattern includes a susceptibility code to indicate any antibiotic to which the identified organism is non-susceptible (i.e., has antibiotic resistance) as determined from the subject sample. Some non-limiting examples of susceptibility codes are shown below in TABLE 4:

TABLE 4

| Antibiotic (Resistance) | Susceptibility Code |
|---|---|
| Cefepime | CFP |
| Ceftazidime | CTD |
| Doripenem | DPN |
| Ertapenem | EPN |
| Imipenem | IPN |
| Meropenem | MPN |

A pattern for a resistome profile may be generated to include any combination of the codes described herein as well as additional information. The pattern may be stored, transmitted, and/or displayed in any permutation, including, but not limited to, a list of codes. The codes may be stored, transmitted, and/or displayed in a designated order, separated by a first type of character or symbol, and/or identified by unique code-specific characters or symbols. Where a pattern includes more than one code of the same type (e.g., a plurality of genotype codes), the plurality of codes of that type may be stored, transmitted, and/or displayed in a designated order, separated by a second type of character or symbol, and/or also identified by unique code-specific characters or symbols.

In some embodiments, a pattern is stored, transmitted, and/or displayed such that the codes are separated by a first character or symbol (e.g., a colon) and multiple codes of a type are separated by a second character or symbol (e.g., an underscore). Some non-limiting examples of resistome profiles generated for subjects based on the rules described herein are shown below in TABLE 5:

TABLE 5

| Organism Species | Antibiotic Bacterial Phenotype | Antibiotic Resistance Gene Family | Profile Uniqueness | | Resistome Profile |
| | | | Unique Profile No. | Organism No. | |
| --- | --- | --- | --- | --- | --- |
| E. coli | Carbapenem-resistant Enterobacteriaceae | KPC and OXA-48 | 64 | 3 | E1:CRE:KPC_O48:64-3 |
| K. pneumoniae | Carbapenem-resistant Enterobacteriaceae | VIM and CTX-M-1 | 4 | 1 | K1:CRE:VIM_C1:4-1 |

In the examples in TABLE 5, the patterns (E1:CRE:KPC_O48 and K1:CRE:VIM_C1, respectively) are generated based on organism identification codes (E1 and K1, respectively) indicating organism species identified from subject samples, a phenotype code (CRE) indicating an organism antibiotic susceptibility phenotype determined from subject samples, and genotype codes (KPC and O48, and VIM and C1, respectively) indicating the presence of antibiotic resistance genes as determined from subject samples. For the first subject, the pattern derived is E1:CRE:KPC_O48, reflecting an organism identification code of E1 (indicating E. coli), a phenotype code of CRE (indicating Carbapenem-resistant Enterobacteriaceae), and a genotype codes of KPC and O48 (indicating KPC and OXA-48 gene families), each pattern component derived based on measurement data from a sample from the first subject. For the second subject, the pattern derived is K1:CRE:VIM_C1, reflecting an organism identification code of K1 (indicating K. pneumoniae), a phenotype code of CRE (indicating Carbapenem-resistant Enterobacteriaceae), and a genotype codes of VIM and C1 (indicating VIM and CTX-M-1 gene families), each pattern component derived based on measurement data from a sample from the second subject.

Based on an application of a similarity metric, as described further herein, in comparing each pattern to known patterns from previously classified subjects, profile uniqueness identifiers may be assigned to indicate the uniqueness of each pattern (i.e., the Unique Profile No.) and the number of known patterns (No. of Organisms) that share the pattern or a sufficiently similar pattern. A common infectious source or pathogen transmission route may be identified if organisms from multiple subjects are identified that share a similar resistome profile, such as E1:CRE:KPC_O48:64-34, where profile uniqueness identifier component i (the number of known patterns) differs for each resistome profile. Where genome sequence data is available, the profile uniqueness identifier component i further may include a nearest neighbor indicator representative of the number nucleotides difference from nearest neighbors (including an indication of the location of these differences in the sequences).

According to some embodiments, the resistome profiles in TABLE 5 include the patterns (E1:CRE:KPC_O48 and K1:CRE:VIM_C1, respectively) and the associated profile uniqueness identifiers (64-3 and 4-1, respectively). For the first subject, the pattern (E1:CRE:KPC_O48) is compared to known patterns, for example, in a database and according to a similarity metric, assigned a profile uniqueness identifier of 64-3, indicating that the pattern has already been assigned Unique Profile No. 64 and has been observed three times in total (i.e., two of the known patterns in the database share this pattern or a sufficiently similar pattern). For the second subject, the pattern (K1:CRE:VIM_C1) is compared to known patterns, for example, in the same database and according to the same similarity metric, assigned a profile uniqueness identifier of 4-1, indicating that the pattern is being assigned Unique Profile No. 4 and is being observed for the first time (i.e., none of the known patterns in the database share this pattern or a sufficiently similar pattern).

TABLE 6 below provides other non-limiting examples of resistome profiles generated for subjects based on the rules described herein.

TABLE 6

| Organism Species | Antibiotic Resistance Gene Family | Antibiotic (Resistance) | Profile Uniqueness Unique | | Resistome Profile |
| | | | Profile No. | Organism No. | |
| --- | --- | --- | --- | --- | --- |
| S. marcescens | VIM | Doripenem and Meropenem | 27 | 2 | S1:VIM:DPN_MPN:27-2 |
| A. baumannii | OXA-51 and OXA-23 | Doripenem, Ertapenem, and Meropenem | 88 | 12 | A1:O51_O23:DPN_EPN_MPN:88-12 |

In the examples in TABLE 6, the patterns (S1:VIM:DPN_MPN and A1:O51_O23:DPN_EPN_MPN, respectively) are generated based on organism identification codes (S1 and A1, respectively) indicating organism species identified from subject samples, a genotype code (VIM, and O51 and O23, respectively) indicating an antibiotic resistance gene family determined from subject samples, and susceptibility codes (DPN and MPN, and DPN, EPN, and MPN, respectively) indicating antibiotics to which the subject samples show resistance. For the first subject, the pattern derived is S1:VIM:DPN_MPN, reflecting an organism identification code of S1 (indicating S. marcescens), a genotype code of VIM (indicating the presence of the VIM gene family), and the susceptibility codes of DPN and MPN (indicating resistance to Doripenem and Meropenem), each pattern component derived based on measurement data from a sample from the first subject. For the second subject, the pattern derived is A1:O51_O23:DPN_EPN_MPN, reflecting an organism identification code of A1 (indicating *A. baumannii*), genotype codes of O51 and O23 (indicating the OXA-51 and OXA-23 gene families), and the susceptibility codes of DPN and MPN (indicating resistance to Doripenem, Ertapenem, and Meropenem), each pattern component derived based on measurement data from a sample from the second subject.

Based on an application of a similarity metric, as described further herein, in comparing each pattern to known patterns from previously classified subjects, profile uniqueness identifiers may be assigned to indicate the uniqueness of each pattern and the number of known patterns that share the pattern or a sufficiently similar pattern. According to some embodiments, the resistome profiles in TABLE 6 include the patterns (S1:VIM:DPN_MPN and A1:O51_O23:DPN_EPN_MPN, respectively) and the associated profile uniqueness identifiers (27-2 and 88-12, respectively). For the first subject, the pattern (S1:VIM:DPN_MPN) is compared to known patterns, for example, in a database and according to a similarity metric, assigned a profile uniqueness identifier of 27-2, indicating that the pattern has already been assigned Unique Profile No. 27 and has been observed once before (i.e., one of the known patterns in the database shares this pattern or a sufficiently similar pattern). For the second subject, the pattern (A1:O51_O23:DPN_EPN_MPN) is compared to known patterns, for example, in the same database and according to the same similarity metric, assigned a profile uniqueness identifier of 88-12, indicating that the pattern is being assigned Unique Profile No. 88 and has been observed twelve times now (i.e., eleven of the known patterns in the database share this pattern or a sufficiently similar pattern).

The resistome profiles also may be generated based on additional database information, including, but not limited to, metadata, that is not included in TABLES 5 and 6. For example, a nearest neighbor indicator representative of the number of nucleotides differences from nearest neighbors (including locations of those differences in the nucleotide sequences) may be obtained from genome sequence data. The nearest neighbor indicator may be included as a component of the profile uniqueness identifier (e.g., as a third number), or may be included in the resistome profile as a separate classification parameter.

Other metadata that may be available and/or used includes, but is not limited to, at least one of a facility indication (e.g., a descriptive name, such as "Pasteur"), a known gene (e.g., "NAP07"); a geographic location or region (e.g., where an organism was first identified, such as "Europe," "Philippines," "California," or "Toronto"), one or more gene polymorphisms (e.g., spa typing nomenclature, such as "ClaI-MecA polymorphisms:ClaI-Tm554 patterns:SmaI-PFGE restriction profiles"), and a series of symbols to describe spa types (e.g., numbers or letters, such as "WGKAKBAOKAOMQ," where each letter corresponds to a different polymorphism of a 24-base pair repeat).

Similarity Metrics

In some embodiments, as described above with respect to step 214 of FIG. 2, a first pattern obtained from a subject is compared with a plurality of known patterns from previously classified subjects to identify a degree of similarity, if any, between the first pattern and one or more of the known patterns. A similarity metric may be applied to compare the first pattern to each of the known patterns such that a profile uniqueness identifier may be assigned to the pattern and a resistome profile may be generated based on at least the first pattern and the profile uniqueness identifier. For example, a profile uniqueness identifier may reflect whether the degree of similarity is determined to be above a predetermined threshold between the first pattern and one or more known patterns.

In other embodiments, a first resistome profile is compared with a plurality of candidate resistome profiles from previously classified subjects to identify a degree of similarity, if any, between the first resistome profile and one or more of the candidate resistome profiles. A similarity metric may be applied to compare the first resistome profile to each of the candidate resistome profiles such that an outbreak of infection (e.g., at a facility) may be identified.

In some embodiments, the similarity metric is configured to compare patterns and/or resistome profiles to detect similarity on an exact match basis and classify detected similarity using binary rules. For example, if two patterns have coded notations indicating the same species (e.g., based on data from an identification test), the same resistance genes (e.g., based on data from a MDRO test), and/or the same antibiotic susceptibility (e.g., based on data from an AST), then the isolate samples may be designated as having matching patterns according to a similarity metric.

In some embodiments, the profile uniqueness code reflects pattern matching. A first part of a profile uniqueness code may indicate a uniqueness of a first pattern compared to one or more known patterns (i.e., the absence of a degree of similarity above a threshold). A second part of a profile uniqueness code may indicate how many known profiles share a sufficiently similar pattern (i.e., have a degree of similarity above a threshold). For example, if two patterns are sufficiently similar (comparing, e.g., the character string codes or additional information), the first part of each profile uniqueness code will be the same. If the samples came from different subjects, then the second part of the respective profile uniqueness codes (i.e., the patient count or "number of organisms" with a sufficiently similar patterns) will be different (e.g., incremented by one).

On the other hand, if one or more components of a pattern and/or resistome profile differ from a known pattern and/or resistome profile, the pattern and/or resistome profile may be designated/classified as different depending on a threshold determined or predetermined for the applied similarity metric. The threshold may depend on, for example, a ranking of clinical importance associated with different pattern and/or profile components.

In the non-limiting sample examples Ex. 7A, Ex. 7B, Ex. 8A, and Ex. 8B shown below in TABLES 7 and 8, all of the samples include the organism *Serratia marcescens* (organism identification code S1) and have a common antibiotic bacterial phenotype of Carbapenem-resistant Enterobacteriaceae (phenotype code CRE); however, Ex. 7A and Ex. 7B, and Ex. 8A and Ex. 8B, respectively, differ in genotype. That is, although the genotypes of all the samples include gene families NDM and OXA(C), the genotypes of Ex. 7B and Ex. 8B also includes gene families of the genotype CTX-M(A).

TABLE 7

| Ex. | Species | Phenotype | Genotype | Resistome Profile |
|---|---|---|---|---|
| 7A | S1 | CRE | NDM, OXA(C) | S1:CRE:NDM_O48:1-1 |
| 7B | S1 | CRE | NDM, OXA(C), CTX-M(A) | S1:CRE:NDM_O48:2-1 |

Thus, the pattern notations assigned to the resistome profiles of all the samples are the same (S1:CRE: NDM_O48), but differences recognized during application of the similarity metric still may cause the two resistome profiles to be classified differently (e.g., with profile uniqueness identifiers). In TABLE 7, Ex. 7A is designated/classified with profile uniqueness identifier 1-1, while Ex. 7B is designated/classified with profile uniqueness identifier 2-1. The first digit of the profile uniqueness identifier indicates the uniqueness of the samples in spite of a matching pattern notation, thereby designating/classifying the resistome profiles as different from each other. The second digit of the profile uniqueness identifier indicates that both resistome profiles are being observed for the first time.

TABLE 8

| Ex. | Species | Phenotype | Genotype | Resistome Profile |
|---|---|---|---|---|
| 8A | S1 | CRE | NDM, OXA(C) | S1:CRE:NDM_O48:1-1 |
| 8B | S1 | CRE | NDM, OXA(C), CTX-M(A) | S1:CRE:NDM_O48:1-2 |

In another example, the patterns of the two samples Ex. 8A and Ex. 8B may be designated as a match based on a classification rule of a similarity metric that sets rankings for profile components based on clinical importance. That is, according to some embodiments, two patterns that differ by a pattern or profile component (e.g., drug resistance genotype) ranked as having a low clinical importance score still may be designated/classified as a match. Therefore, if the inclusion of CTX-M(A) in the genotype of Ex. 8B is determined to have relatively less clinical importance according to the similarity metric, then the pattern notations may be designated/classified as a match. As shown in TABLE 8, Ex. 8A may be designated with profile uniqueness identifier 1-1, while Ex. 8B is designated with profile uniqueness identifier 1-2. The first digit of each profile uniqueness identifier indicates that the samples are designated/classified as a match. Assuming that Ex. 8A and Ex. 8B are from different samples/subjects, the second digit of the profile uniqueness identifier for Ex. 8A indicates that the pattern is being observed for the first time, and the second digit of the profile uniqueness identifier for Ex. 8B indicates that this is the second observation of this pattern.

While variations in similarity metrics may result in the same or similar treatments for an individual subject, the classification of a facility or subject population as to a potential outbreak may change based on different similarity metrics according to some embodiments. For example, a facility or population may be classified as at risk or not at risk for a potential outbreak precisely because of these types of differences in genotypes reflected in Ex. 7A, Ex. 7B, Ex. 8A, and Ex. 8B.

Higher resolution data, including, but not limited to, sequencing data, may be available and be incorporated into the pattern generation engine used to assign the resistome profile. For example, a similarity metric may be configured to search for one or more nucleotide differences. The similarity metric also may be configured to search for the locations of those differences in the sequence, as described herein in connection with the nearest neighbor determination. Any existing technique or tool used for sequence comparison/alignment may be applied to the sample data to determine similarity. For example, similarity information may be extracted from similarity diagrams. The sequence alignment stringency of the similarity metric may be adjustable or set differently based on the type of organism or the sample conditions. In some embodiments, a similarity metric may be configured to generate an alignment score based, for example, on the degree of alignment and/or the sequence difference locations.

Infection States

Figure 3:
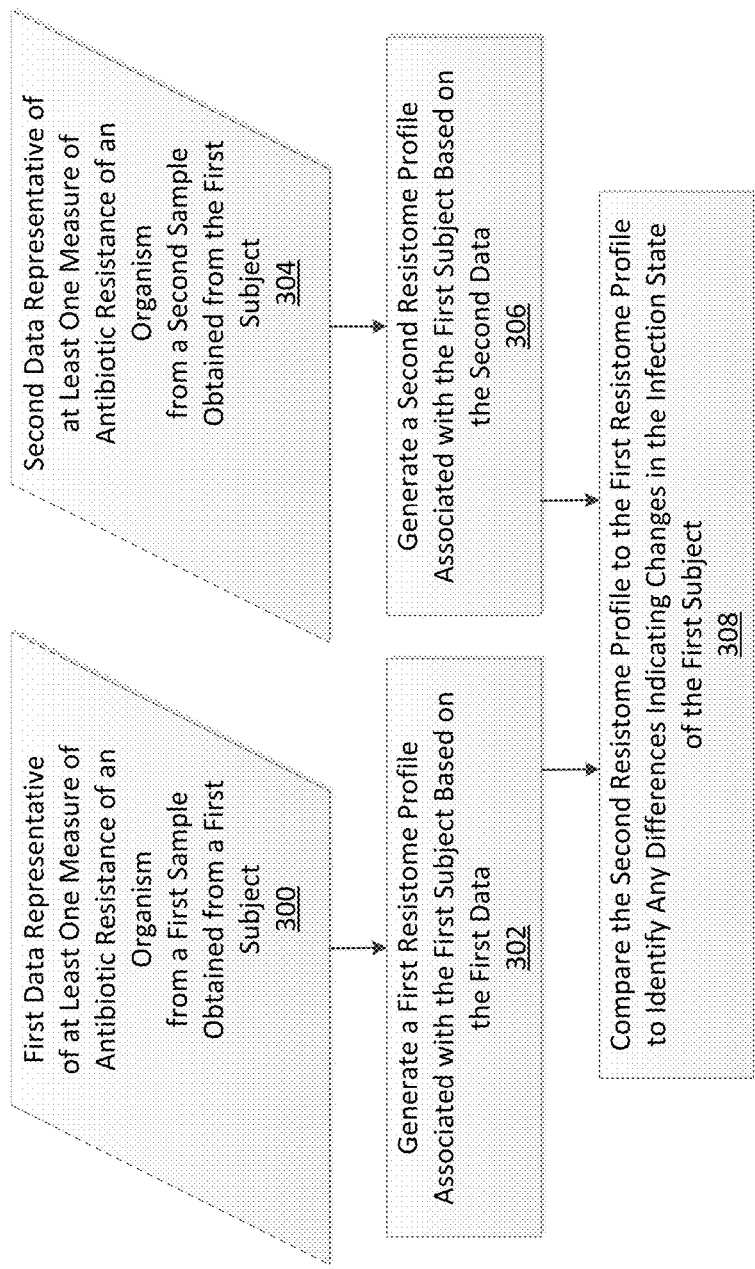
FIG. 3 is a flowchart illustrating a method for monitoring an infection state of a subject in accordance with some embodiments.

FIG. 3 is a flowchart illustrating a method for monitoring an infection state of a subject according to some embodiments. In step 300, first data representative of at least one measure of antibiotic resistance of an organism in a first sample from a subject is obtained. At least one organism in the sample may be identified from the data using, for example, molecular weight profiles and/or mass spectrometry measurements (e.g., MALDI TOF). An antibiotic susceptibility phenotype, an antibiotic resistance gene, and/or an antibiotic to which the organism is non-susceptible also may be determined from the data. A first pattern associated with the first sample may be generated based on the identified organism and at least one of the determined antibiotic susceptibility phenotype, the determined antibiotic resistance gene, and the determined antibiotic to which the organism is non-susceptible. The first pattern may include an organism identification code and at least one of a phenotype code, a genotype code, and a susceptibility code. A similarity metric may be applied to compare the first pattern to a plurality of known patterns from previously classified subjects. If a degree of similarity between the first pattern and any of the known patterns exceeds a threshold, a first profile uniqueness identifier may be assigned to the first sample from the subject.

In step 302, a first resistome profile is generated for the subject based on the first data representative of the first sample derived from the subject. The first resistome profile may include the first pattern and the first profile uniqueness identifier.

In step 304, second data representative of at least one measure of antibiotic resistance of an organism in a second sample from the subject is obtained. A second pattern associated with the second sample may be generated, a similarity metric may be applied to compare the second pattern to a plurality of known patterns from previously classified subjects. If a degree of similarity between the second pattern and any of the known patterns exceeds a threshold, a second profile uniqueness identifier may be assigned to the second sample from the subject.

In step 306, a second resistome profile is generated for the subject based on the second data representative of the second sample derived from the subject. The second resistome profile may include the second pattern and the second profile uniqueness identifier.

In step 308, the second resistome profile is compared to the first resistome profile to identify any differences. A similarity metric may be applied to compare the second profile to the first profile and determine any differences, depending on a threshold determined or predetermined for the applied similarity metric. The threshold may depend on, for example, a ranking of clinical importance associated with different profile components. Differences between the first resistome profile and the second resistome profile may indicate a change in the infection state of the subject.

According to some embodiments, a facility may implement the method of FIG. 3 to monitor a subject's infection state over time. For example, in a diagnosis or treatment facility, a plurality of samples may be obtained from a patient over the course of a single visit or stay with the facility or over separate visits to the facility and compared for indications of changes in the patient's infection state. In some embodiments, a course of treatment for a subject may be determined, or modified, based on the subject's determined infection state and changes thereof.

Figure 4:
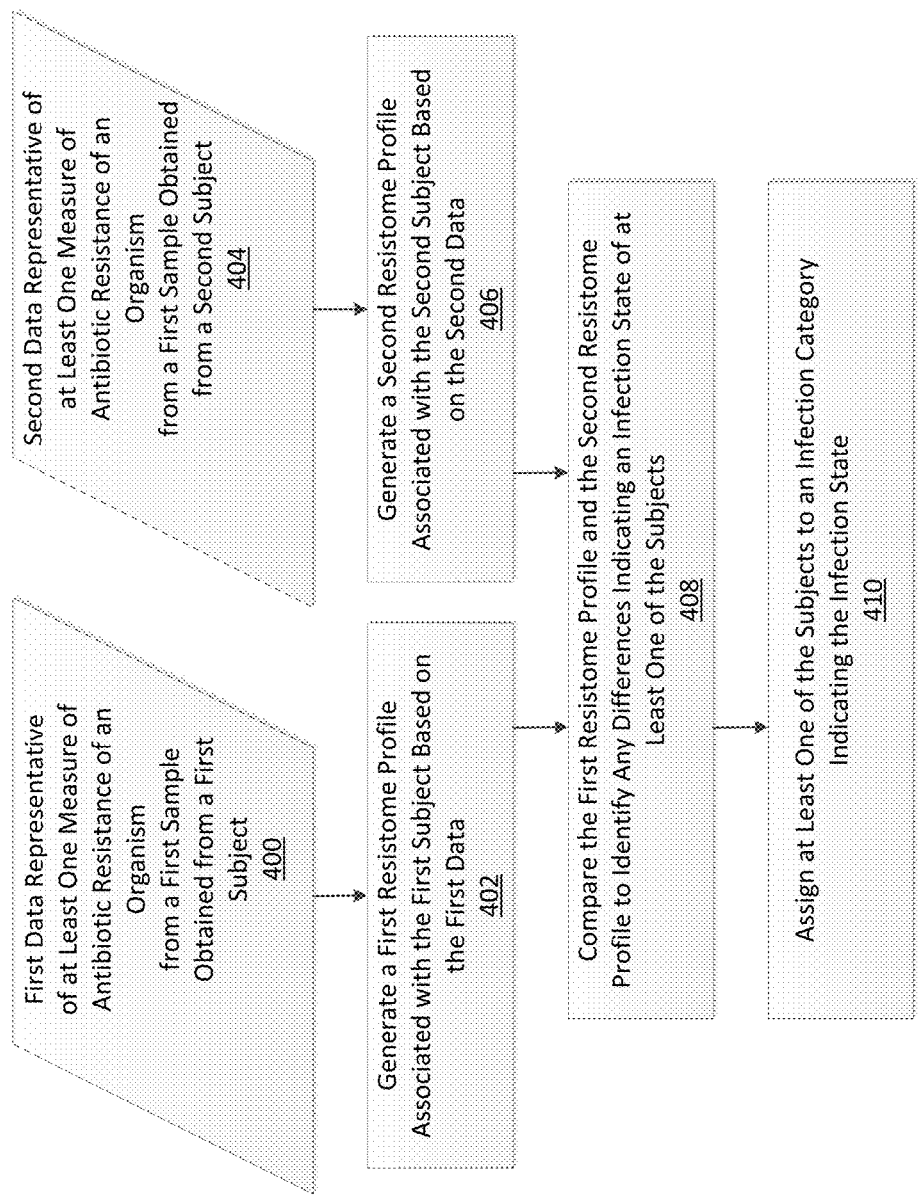
FIG. 4 is a flowchart illustrating a method of determining an infection state in accordance with some embodiments.

FIG. 4 is a flowchart illustrating a method for determining an infection state according to some embodiments. In step 400, first data representative of at least one measure of antibiotic resistance of an organism in a first sample from a first subject is obtained. At least one organism in the sample may be identified from the data using, for example, molecular weight profiles and/or mass spectrometry measurements (e.g., MALDI TOF). An antibiotic susceptibility phenotype, an antibiotic resistance gene, and/or an antibiotic to which the organism is non-susceptible also may be determined from the data. A first pattern associated with the first sample may be generated based on the identified organism and at least one of the determined antibiotic susceptibility phenotype, the determined antibiotic resistance gene, and the determined antibiotic to which the organism is non-susceptible. The first pattern may include an organism identification code and at least one of a phenotype code, a genotype code, and a susceptibility code. A similarity metric may be applied to compare the first pattern to a plurality of known patterns from previously classified subjects. If a degree of similarity between the first pattern and any of the known patterns exceeds a threshold, a first profile uniqueness identifier may be assigned to the first sample from the subject.

In step 402, a first resistome profile is generated for the first subject based on the first data representative of the first sample derived from the subject. The first resistome profile may include the first pattern and the first profile uniqueness identifier.

In step 404, second data representative of at least one measure of antibiotic resistance of an organism in a first sample from a second subject is obtained. A second pattern associated with the first sample from the second subject may be generated, a similarity metric may be applied to compare the second pattern to a plurality of known patterns from previously classified subjects. If a degree of similarity between the second pattern and any of the known patterns exceeds a threshold, a second profile uniqueness identifier may be assigned to the second sample from the subject.

In step 406, a second resistome profile is generated for the second subject based on the second data representative of the first sample derived from the second subject. The second resistome profile may include the second pattern and the second profile uniqueness identifier.

In step 408, the second resistome profile is compared to the first resistome profile to identify any differences indicating an infection state of at least one of the subjects. A similarity metric may be applied to compare the second profile to the first profile and determine any differences, depending on a threshold determined or predetermined for the applied similarity metric. The threshold may depend on, for example, a ranking of clinical importance associated with different profile components. If the infection state of one subject is known (i.e., one subject is assigned to an infection category, wherein the infection category provides an indication of the infection state), differences or similarities between the first resistome profile and the second resistome profile may indicate an infection state of the other subject (i.e., the other subject may be assigned to the same or a different infection category based on the comparison).

In some embodiments, a diagnosis, course of treatment, or assessment of treatment is informed by a determined infection category or infection state. The apparatus 100 of FIG. 1 may be used for monitoring infection states of one or more subjects and/or assigning one or more subjects to an infection category in accordance with some embodiments. For example, apparatus 100 may be used to generate, store, transmit, and/or display resistome profiles for a plurality of samples from the subject. In some embodiments, the at least one processor 106 includes an infection state classifier, by which the at least one processor 106 executes processor-executable instructions 108 stored in the at least one memory 104 to determine an infection state of one or more subjects based on one or more resistome profiles generated according to any of the principles described herein. The indication of the infection state of the one or more subjects may be stored as data 110 on the at least one memory 104 or may be stored externally to the apparatus, e.g., at an external device 114, 116 (which may include cloud data storage). The at least one processor 106 also may execute processor-executable instructions 108 to control the communication interface 102 to communicate to the external device 114, 116 and/or control the memory 104 to store resistome profiles and/or infection state classifications.

Systems, apparatus, and methods also may be used to create and maintain at least one database and informatics interface according to the principles herein. A database and informatics interface may have pro-active alert capabilities to identify and/or monitor emerging trends of transmission with high resolution for antibiotic resistance patterns.

Potential Infection Outbreaks

Figure 5:
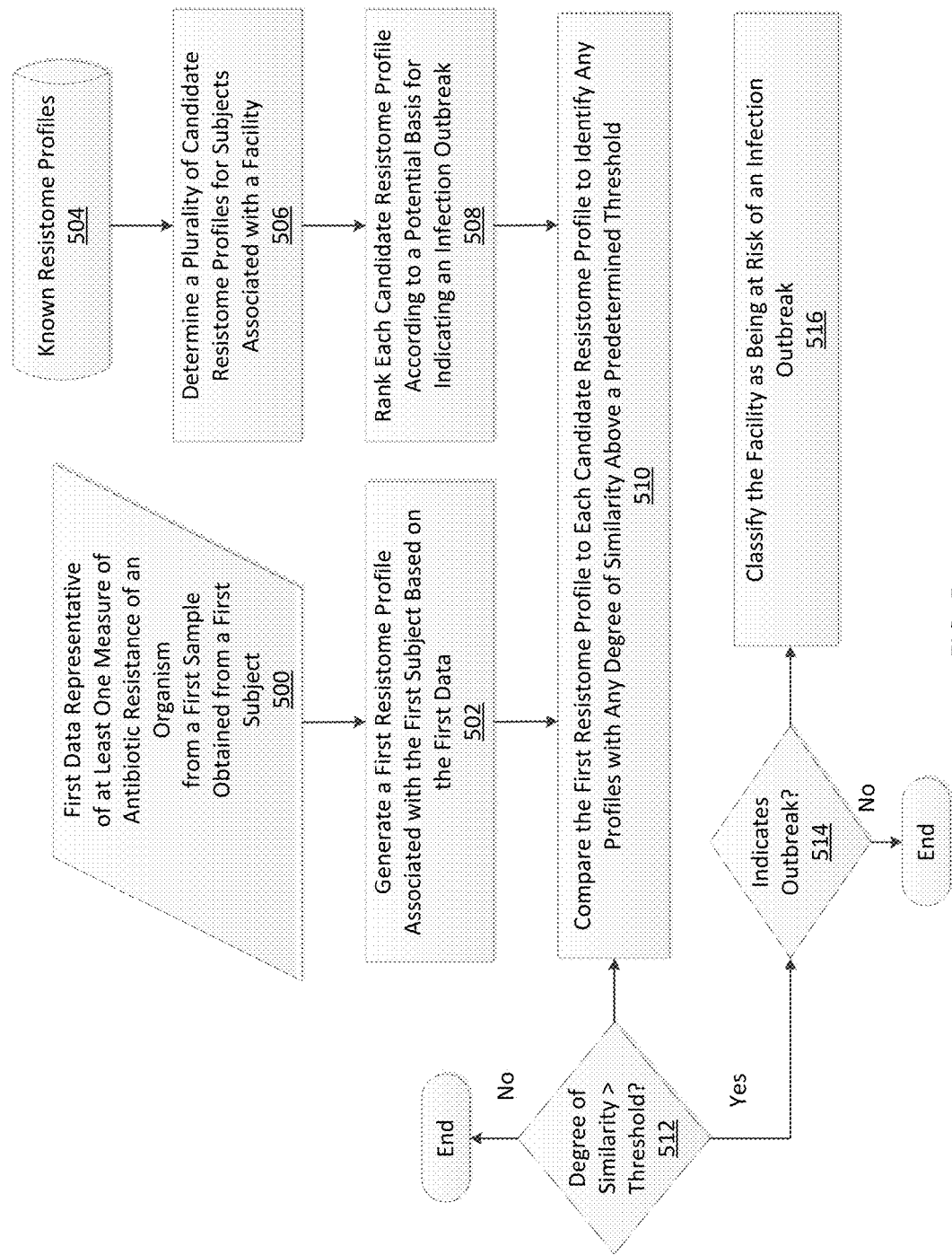
FIG. 5 is a flowchart illustrating a method for identifying a potential infection outbreak in accordance with some embodiments.

FIG. 5 is a flowchart illustrating a method for identifying a potential infection outbreak in a subject population according to some embodiments. In step 500, first data representative of at least one measure of antibiotic resistance of an organism in a first sample from a first subject is obtained.

In step 502, a first resistome profile is generated for the first subject based on the first data representative of the first sample derived from the subject. The first resistome profile may include the first pattern and the first profile uniqueness identifier.

A plurality of known patterns from previously classified subjects 504 may be accessed in step 506 to identify a plurality of candidate resistome profiles for subjects of the population or associated with the population (e.g., a facility). The plurality of candidate resistome profiles may be stored in one or more databases across one or more devices. Each candidate resistome profile of the plurality of candidate resistome profiles corresponds to a previously classified subject (e.g., a subject that is known to have been associated with the facility). For example, a previously classified subject may be considered to be or have been associated with the facility if the subject is currently being treated at the facility, was previously treated at the facility, visited the facility within a certain period of time (e.g., a time interval equal to the incubation period of an infection), or came into physical contact or was within a certain proximity of another individual who is currently being treated at the facility, was previously treated at the facility, or visited the facility within a certain specified period of time. This certain specified period of time may be set based on an average incubation period of an infection or on another clinical measure specified by a user.

In step 508, each candidate resistome profile corresponding to a previously classified subject is ranked according to a potential basis for indicating an infection outbreak. In some embodiments, the candidate resistome profiles may be already associated with a rank that indicates a basis (i.e., likelihood) for indicating an infection outbreak. Some bacterial organisms may be ranked as potentially dangerous or deadly bacteria. Non-limiting examples of these bacteria include carbapenem-resistant Enterobacteriaceae (CRE)

containing KPC, NDM-1, and OXA-48 genes. These bacteria are resistant to nearly all antibiotics, including carbapenems (a broad spectrum class of antibiotics used to treat Gram-negative bacterial infections).

For example, a candidate resistome profile that includes the phenotype code CRE (for carbapenem-resistant Enterobacteriaceae) may be ranked as having a potentially high basis for indicating an infection outbreak. In a further example, a candidate resistome profile that includes the phenotype code CRE and a genotype code for at least one of a KPC, an NDM-1, and an OXA-48 gene, may be ranked as having a relatively higher basis for indicating an infection outbreak, and a candidate resistome profile that includes the phenotype code CRE, and a genotype code for a KPC gene may be ranked as having an even higher basis for indicating an infection outbreak.

In step 510, the first resistome profile is compared to each candidate resistome profile. In step 512, it is determined whether a degree of similarity above a threshold exists between the first resistome profile and each candidate resistome profile. If there is no degree of similarity or at least not a sufficient degree of similarity (above the threshold), the process ends. However, if there is a degree of similarity above the threshold, in step 514, it is determined whether an infection outbreak is indicated, for example, based on whether any candidate resistome profiles with sufficient similarity is ranked as potentially indicating an infection outbreak. If no candidate resistome profile with sufficient similarity is ranked as potentially indicating an infection outbreak, the process ends. However, if at least one candidate resistome profile with sufficient similarity is ranked as potentially indicating an infection outbreak, then in step 516, the population (e.g., the facility) is classified as being at risk of an infection outbreak.

The apparatus 100 of FIG. 1 may be used for identifying a potential infection outbreak in a subject population according to some embodiments. For example, apparatus 100 may be used to generate, store, transmit, and/or display resistome profiles for a plurality of samples from the subject. In some embodiments, the at least one processor 106 includes an outbreak classifier, by which the at least one processor 106 executes processor-executable instructions 108 stored in the at least one memory 104 to determine a potential for an infection outbreak based on a plurality of resistome profiles generated for a plurality of subjects according to any of the principles described herein. Information indicating an outbreak classification may be stored as data 110 on the at least one memory 104 or may be stored externally to the apparatus, e.g., at an external device 114, 116 (which may include cloud data storage). The at least one processor 106 also may execute processor-executable instructions 108 to control the communication interface 102 to communicate to the external device 114, 116 and/or control the memory 104 to store resistome profiles and/or information indicating an outbreak classification, such as for a population or facility.

Information indicating an outbreak classification may be stored or output via a network or displayed to a user as a code notation. For example, information indicating an outbreak classification may be stored, transmitted, and/or displayed as a character string representation of the resistome profile(s) that contributed to the classification or as a user-specified notation (e.g., using a lookup table), as described further herein. In some embodiments, information indicating an outbreak classification is displayed to a user as a graphical representation, including, but not limited to, a two-dimensional code (e.g., a QR code), a tube graph, and an epidemiology star chart.

Gene Detection

In some embodiments, apparatus 100 includes, is a component of, or is connected to a at least one gene detection system and analysis platform. The at least one gene detection system may be a multi-drug resistant organism (MDRO) gene detection system. Based on data collected from analysis of a sample from a subject using the at least one gene detection system and information associated with the subject from whom the sample was obtained, a resistome profile associated with the subject may be generated according to the principles described herein. The data representative of a measure of antibiotic resistance of an organism in the sample obtained from the subject includes at least a portion of the data collected from the analysis of the sample using the gene detection system. A non-limiting example of an MDRO gene detection system is disclosed in U.S. Provisional Application No. 61/952,795, filed on Mar. 13, 2014, titled "Methods of Detecting Multi-Drug Resistant Organisms," the disclosure of which is incorporated herein by reference in its entirety.

Figure 6:
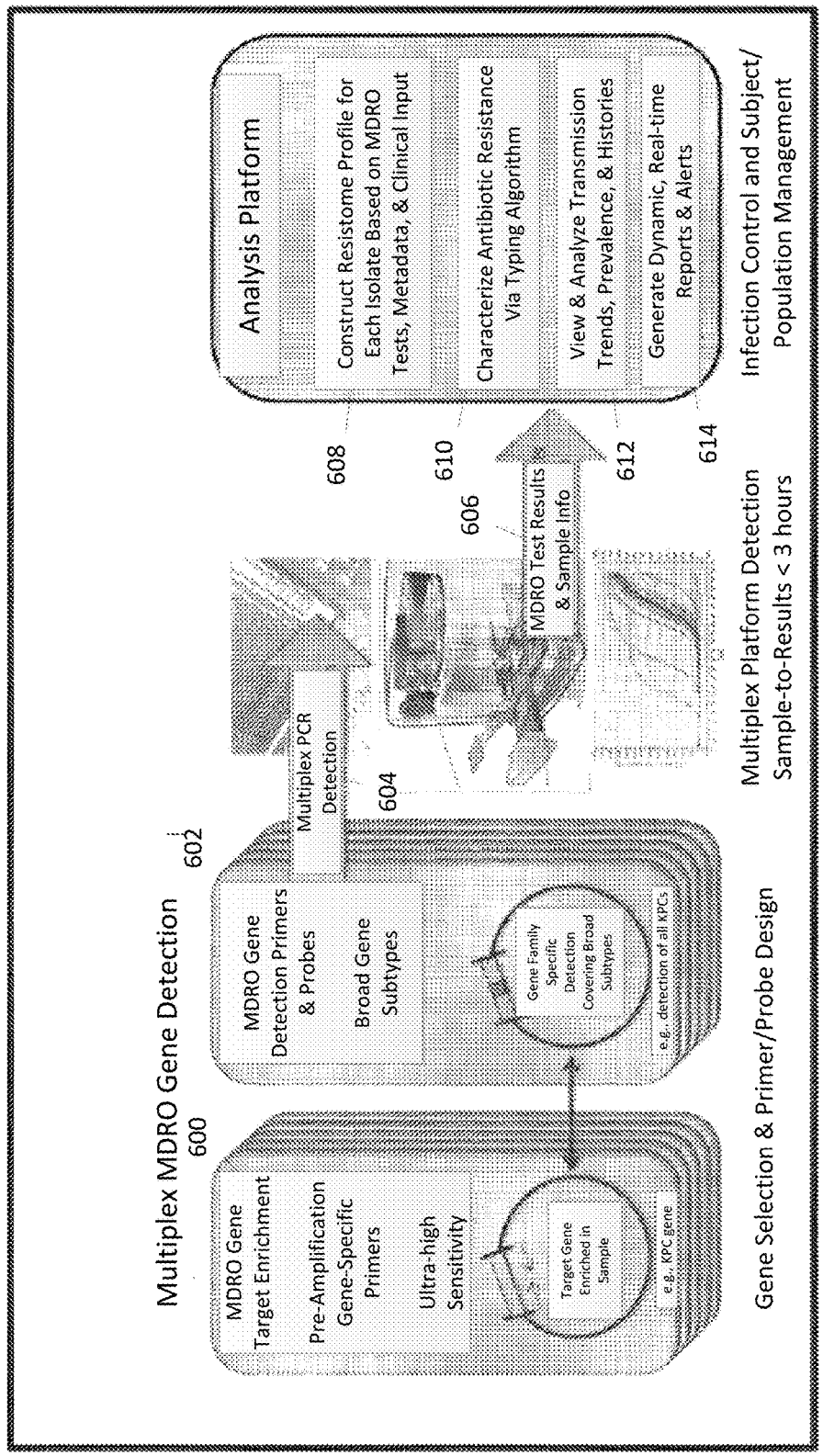
FIG. 6 is a block diagram illustrating a gene detection system and analysis platform in accordance with some embodiments.

FIG. 6 is a block diagram illustrating a gene detection system and method for generating a resistome profile of a subject in accordance with some embodiments. For example, a subject may be suspected of or at high risk for having a MDRO colonization or infection. High risk human subjects include, but are not limited to, patients residing in or being admitted from a long-term care facility, patients admitted to Intensive Care Units (ICUs), immuno-compromised patients, patients being treated for cancer or undergoing chemotherapy, organ and bone marrow transplant patients, patients with ventilators or catheters, patients in preparation for surgical procedures, postsurgical patients, patients previously diagnosed or treated for a Healthcare-Associated Infection (HAI), and others. Particularly high risk patients are neutropenic, have cancer, or have received a transplant. In some aspects a patient may be asymptomatic (not exhibiting the traditional signs and symptoms) but still be at high risk, colonized, or infected.

In particular, FIG. 6 includes a multiplex MDRO gene detection system (e.g., the ACUITAS™ MDRO Gene Test System), which may be used to contribute to the sample data utilized by the systems, apparatus, and methods described herein. For example, an MDRO gene detection system may apply DNA amplification and detection technology to detect genes associated with an identified organism (e.g., bacteria).

According to some embodiments, a Gram-negative or Gram-positive bacteria DNA sample is extracted from a biological sample from a patient. The sample may be any biological sample, including, but not limited to, an anal swab, a rectal swab, a skin swab, nasal swab, wound swab, stool, blood, plasma, serum, urine, sputum, respiratory lavage, cerebrospinal fluid, or an environmental swab. Extraction may be accomplished by any known method or system in the art, including, but not limited to, MagNA Pure™ Systems (available from Roche, Basel, Switzerland). Preferably, extraction both isolates and purifies the DNA sample, such that the DNA sample is substantially free of protein, cellular debris, and PCR inhibitors.

In some embodiments, the systems, apparatus, and methods described herein have format flexibility to discriminate individual gene subtypes, or to screen for all MDRO gene families and subtypes in a combined probe "cocktail" assay format. The systems, apparatus, and methods described herein may provide for an optimal assay system whereby new MDRO genes or subtypes or infectious disease organism molecular biomarkers or identification genes may be incorporated into the assay format, to expand the scope of MDRO screening and identification potential based on the emergence of new MDROs over time.

This ultra-high sensitivity and resolution may be accomplished by combining a pre-amplification step followed by a detection step utilizing primers and probes based upon sequence homology of the MRDO-associated gene families in accordance with some embodiments. The primers and probes may include degenerate primers sequence capable of amplifying and detecting MDRO-associated gene sub-families and subtypes. Based on the level of detection, the primers and probes may provide a semi-quantitative assessment on the level of MDRO genes in the sample. Thus, the methods are not only capable of detecting the presence of a MRDO-associated gene in a sample, the method also provide for the identification and semi-quantitative level of the subtype of the MDRO-associated gene. This ability to provide a genotype allows for the presumptive identification of bacterial species. Thus, an unexpected advantage of the methods is that they provides the clinician with some guidance as to which bacteria species the subject is infected/or colonized with, and provides guidance on the risk profile of the subject for potential conversion from colonization to infection, or potential risk of transmitting a MDRO to another individual. This ability to stratify genotype is also very specific and reproducible. Another, unexpected advantage of the methods is the extreme sensitivity that may be ascertained by using a single swab sample. Unlike other methods know in the art, the methods are capable of detecting less than 210 CFU/sample (and in some instance less than 15 CFU/sample) without the need to culture the sample.

Once the bacterial DNA is extracted from the biological sample, an enrichment step is performed prior to the detection of the MDRO associated genes. Enrichment is accomplished for example by performing multiplex PCR. After enrichment, detection is performed for example by using real time PCR using primers that are specific to the MDRO associated gene being detected. Optionally, an internal amplification control is included to guard against false negatives associated with PCR inhibition. Additionally, appropriate positive, negative, and no-template control (NTC) samples are included during each performance run of the assay.

For example, in block 600 of FIG. 6, a first target MDRO gene (e.g., KPC) is selected, and a sample is enriched for the target MDRO gene. Primers specific to the target MDRO gene are used in pre-amplification for ultra-high sensitivity to the target MDRO gene. In block 602, primers and probes (e.g., a multiplex DNA probe) are designed to detect broad subtypes of the target MDRO gene. In block 604, multiplex PCR detection is performed, with MDRO test results and sample information, as shown in block 606, obtained in less than three hours according to some embodiments. Thus, the systems, apparatus, and methods described herein may yield ultra-high sensitivity and resolution of MDRO-associated genes and throughput in less time at lower cost.

FIG. 6 also shows an analysis platform for generating an outcome (e.g., a resistome profile, infection state, or infection outbreak classification) according to some embodiments as described herein. For example, the analysis platform may use an analysis engine and cloud database technology to extend a gene detection system with databases and advanced analytics. Powerful new capabilities include monitoring and tracking bacterial gene subtypes of antibiotic resistance on global and local levels through the assignment of resistome profiles. In block 608, a resistome profile is constructed for each isolate based on the MDRO test results, metadata, and clinical observations.

The MDRO test results may include DNA sequence data for an entire genome, for targeted regions of a genome, and/or for antibiotic resistance genes of interest. If sequence data is available, a resistome profile may include information indicating differences in the nucleotide sequences from nearest neighbors, including, but not limited to, the number and locations of these differences in the nucleotide sequences. A nearest neighbor indicator may be included in a resistome profile as a component of the profile uniqueness identifier, or may be included in the resistome profile as a separate classification parameter.

In block 610, an antibiotic resistance is characterized according to a typing algorithm, described further herein. In block 612, the resistome profile and type contribute to the larger identification and analysis of trends over time, geographical locations, and other factors. For example, prevalence in a particular location (e.g., a facility) may result automatically in the generation of a dynamic, real-time alert and/or report.

Minimum Inhibitory Concentrations and Resistome Scores

In some embodiments, minimum inhibitory concentrations (MICs) for antibiotics are determined—the levels of MICs including, but not limited to, resistance (R), intermediate (I), or susceptible (S)—and used for genotype/phenotype associations and other forms of matching. For example, MICs of some antibiotics for carbapenem-resistant Enterobacteriaceae are shown in TABLE 9 in accordance with some embodiments.

TABLE 9

CRE MICs

| | Susceptible | Intermediate | Resistant |
|---|---|---|---|
| Current Breakpoints (M100-S22) MIC (μg/mL) | | | |
| Doripenem | ≤1 | 2 | ≥4 |
| Ertapenem | ≤0.5 | 1 | ≥2 |
| Imipenem | ≤1 | 2 | ≥4 |
| Meropenem | ≤1 | 2 | ≥4 |
| Revised (M100-S20) MIC (μg/mL) | | | |
| Cefotaxime | ≤1 | 2 | ≥4 |
| Ceftazidime | ≤4 | 8 | ≥16 |
| Ceftriaxone | ≤1 | 2 | ≥4 |

MICs of some antibiotics for cephalosporin-resistant (3rd or 4th generation) Gram-negative bacillus are shown in TABLE 10 in accordance with some embodiments.

TABLE 10

CephR-GNB MICs
Revised (M100-S20) MIC (μg/mL)

| | Susceptible | Intermediate | Resistant |
|---|---|---|---|
| Cefepime | ≤8 | 16 | ≥32 |
| Ceftazidime | ≤4 | 8 | ≥16 |

In some embodiments, a resistome profile for a sample is converted to a resistome score by assigning respective weights to genes across the entire resistome profile based on associated phenotypes. Higher weights may be assigned to genes of lower antibiotic susceptibility or higher antibiotic resistance (i.e., resistant MICs), and lower weights may be assigned to genes with lower antibiotic resistance or higher antibiotic susceptibility (i.e., resistant MICs). This provides a user with the ability to correlate or illustrate associations between genotypic resistome data and phenotypic antibiotic susceptibility or resistance. For example, FIGS. 7 and 8 exhibit good correlation between Resistome Scores and phenotypic antibiotic susceptibility test results. Resistome Scores also may be weighted by other information, including, but not limited to, genomic and/or pathogenicity information, such as the location of a gene on a plasmid, mobile element, or chromosome, and other factors affecting negative clinical outcomes.

Figure 7:
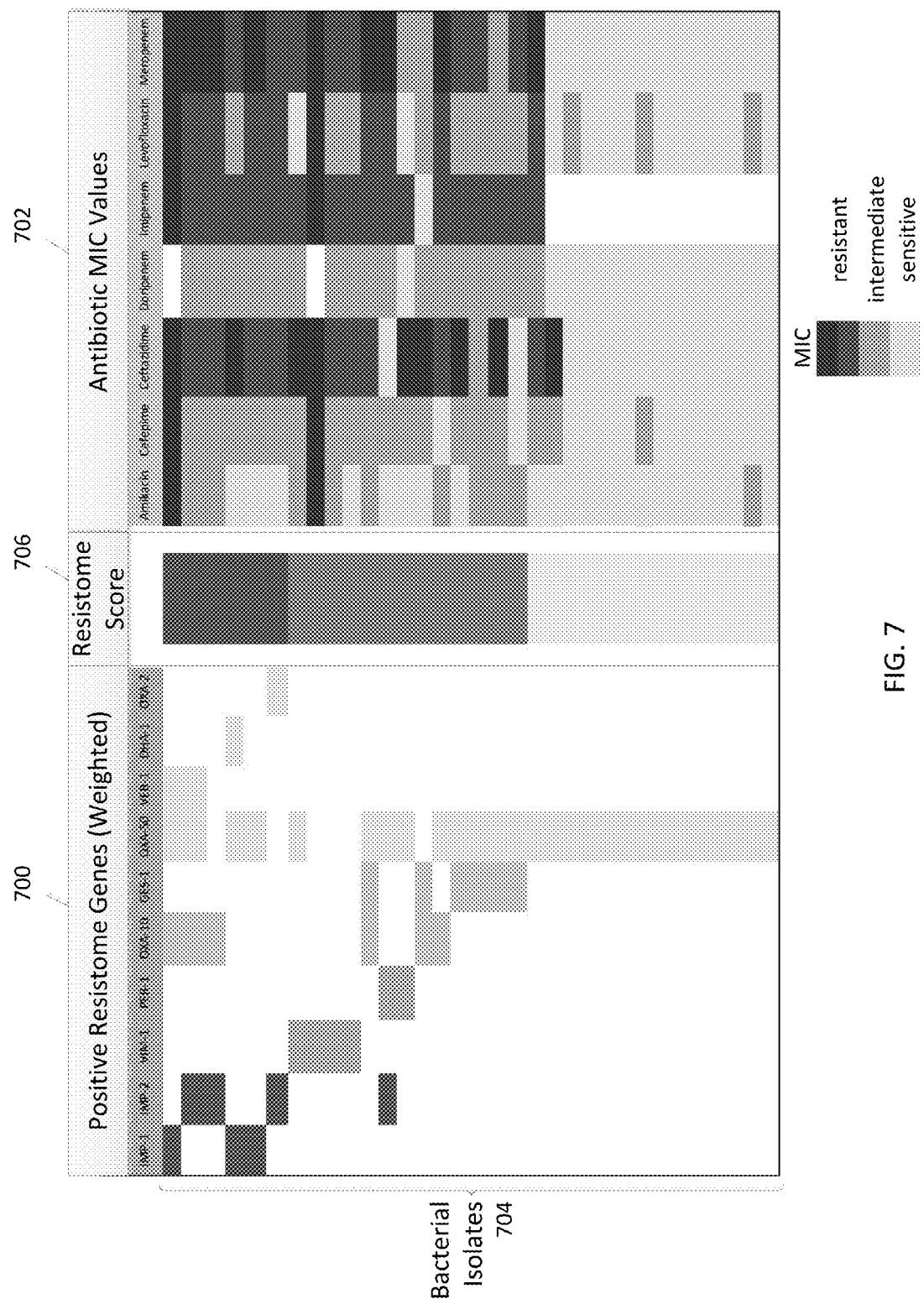
FIGS. 7 and 8 are plots illustrating a resistome test to associate genotypic resistome results and antibiotic susceptibility test results in accordance with some embodiments.

FIG. 7 illustrates associations between genotypic resistome results (e.g., a gene test) 700 and antibiotic susceptibility test results 702 for a set of thirty-three *Pseudomonas aeruginosa* culture isolates. Each row in FIG. 7 represents an individual bacterial isolate 704. The isolates 704 were sorted according to antibiotic susceptibility test results (i.e., phenotypic antibiotic MIC values) 702 with more antibiotic resistant isolates (in darker shades) at the top of the graph. More heavily weighted positive resistome genes are shown (in darker shades) among the genotypic resistome results 700. According to some embodiments, a Resistome Score 706 was calculated for each isolate by weighting each gene 700 in a Resistome Test, with higher scores shown (in darker shades) at the top of the Resistome Score scale 706.

Figure 8:
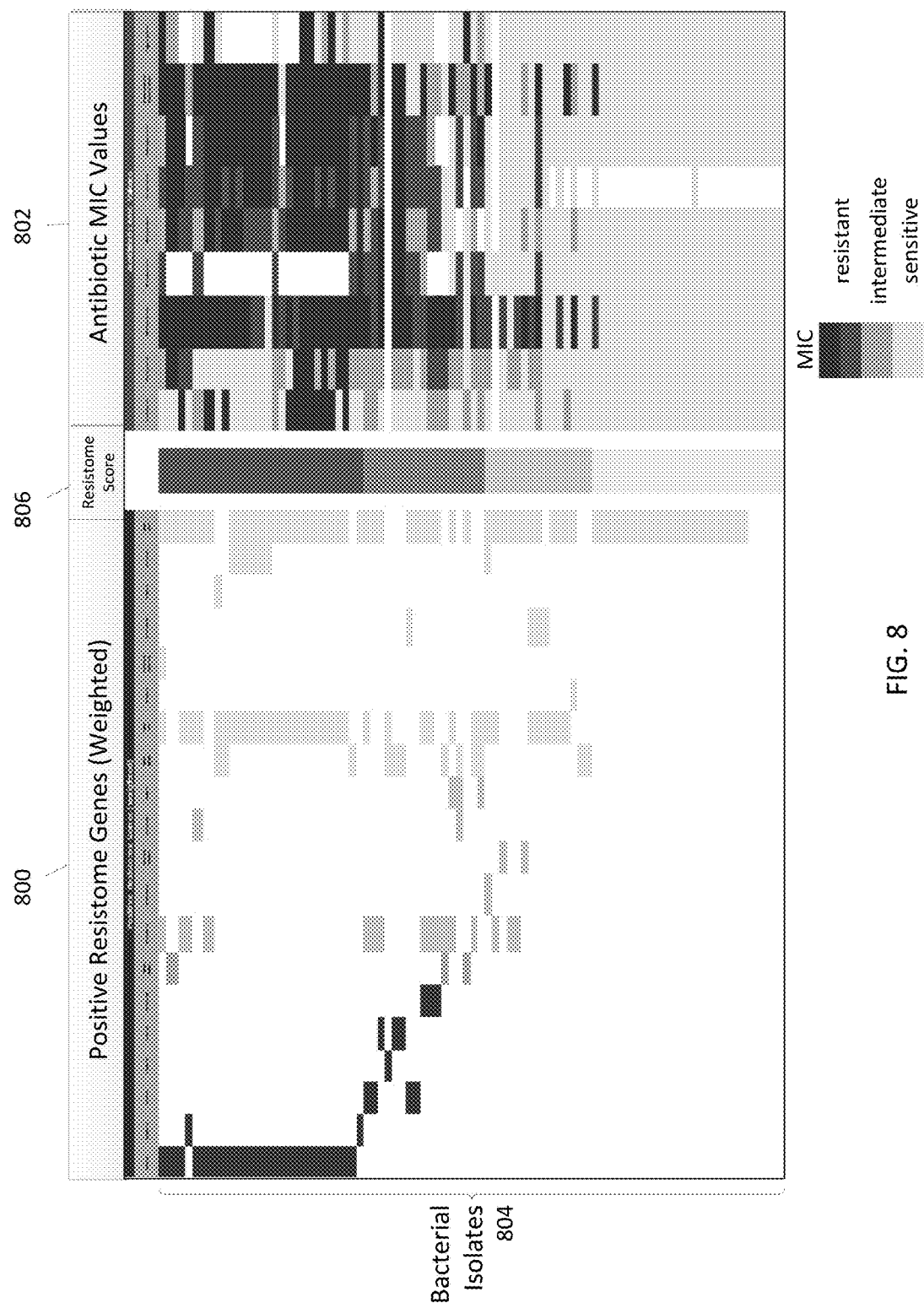

Similarly, FIG. 8 illustrates associations between genotypic resistome results (e.g., a gene test) 800 and antibiotic susceptibility test results 802 for a set of eighty-six *Klebsiella pneumoniae* culture isolates. Each row in FIG. 8 represents an individual bacterial isolate 804. The isolates 804 were sorted according to antibiotic susceptibility test results (i.e., phenotypic antibiotic MIC values) 802 with more antibiotic resistant isolates (in darker shades) at the top of the graph. More heavily weighted positive resistome genes are shown (in darker shades) among the genotypic resistome results 800. According to some embodiments, a Resistome Score 806 was calculated for each isolate by weighting each gene 800 in a Resistome Test, with higher scores shown (in darker shades) at the top of the Resistome Score scale 806. In particular, an isolate that was positive for KPC and CTX-M-1 was assigned a Resistome Score of 1100 through weights of 1000 and 100 for KPC and CTX-M-1, respectively.

Varied Data Classes & Typing

In some embodiments, a resistome profile include various test results or sources of data (i.e., data classes), including results from one or more of a gene test (e.g., MDRO detection), a Resistome Test, identification and antibiotic susceptibility test, sequencing (e.g., whole genome), in silico profiles (e.g., generated from well-documented reference organisms in outbreaks from individual facilities or geographical regions), mass spectrometry (e.g., MALDI-TOF™), phenotype, and sample metadata.

In some embodiments, information gathered from existing systems may be referenced, including information based on at least one of a mass spectrometry spectra (e.g., MALDI-TOF™) database, multi-locus sequence typing (MLST), single nucleotide polymorphism (SNP) schemes, and ribosomal MLST (rMLST). Species-specific MLST may be used as a basis for backwards compatibility reasons. MLST sequence types (ST) may be extracted from next generation sequencing (NGS) data. The pan-bacterial ribosomal MLST may be used. Genome-wide gene by gene bacterial typing (i.e., core genome MLST or MLST+) may be an extension of the traditional MLST concept. These methods may be standardized (in contrast to lineage specific schemes based on explorative SNPs or lineage specific allele typing schemes). Lineage specific SNP/allele approaches may be layered on top of the standardized schemes for local or ad hoc analysis to gain even more discriminatory power.

Figure 9:
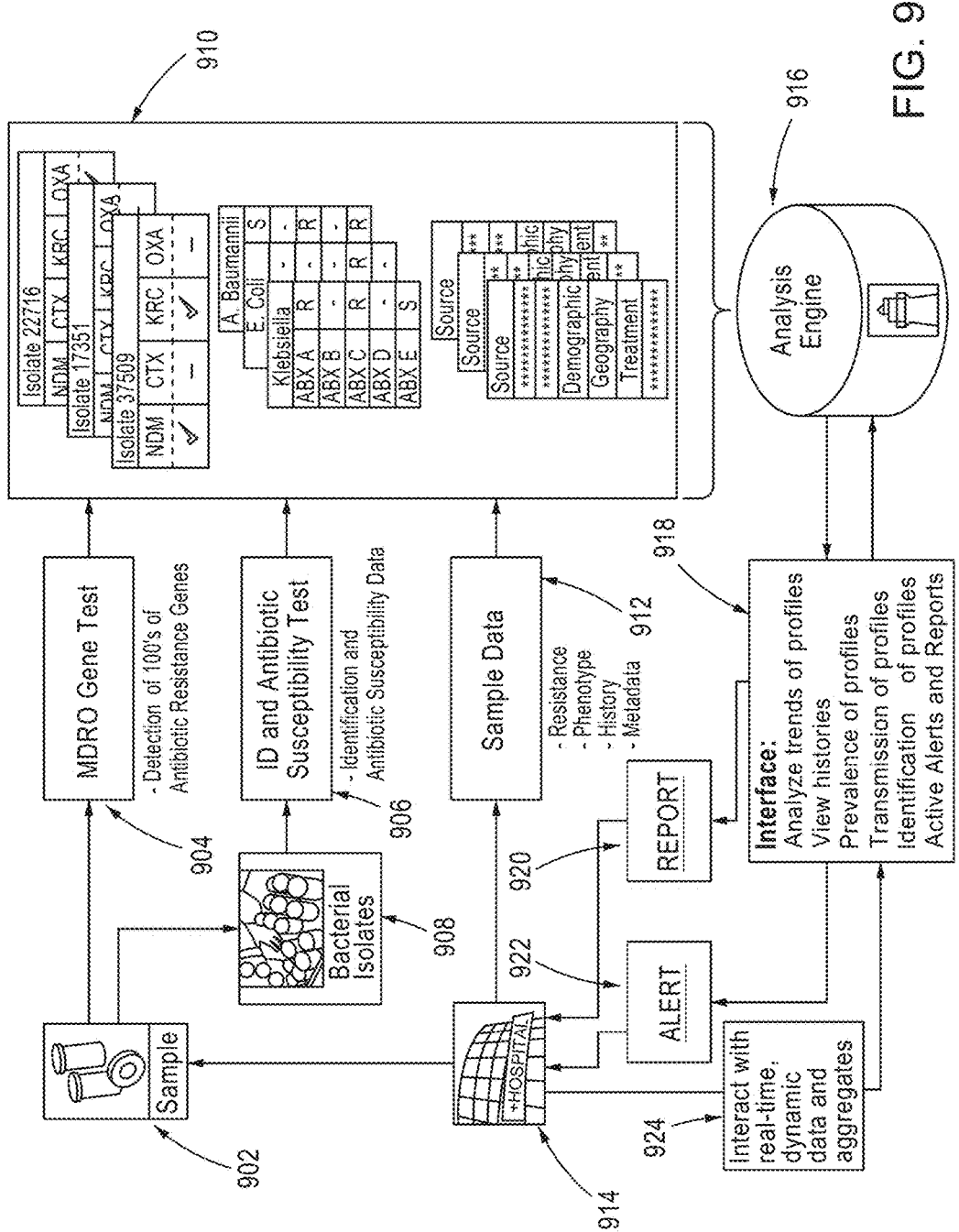
FIG. 9 is a flowchart illustrating methods of using a varied data classes in accordance with some embodiments.

FIG. 9 is a flowchart illustrating methods of using a gene detection system and analysis platform in accordance with some embodiments. Data representative of at least one measure of antibiotic resistance of an organism is obtained from a sample 902 obtained from a subject. The data may be obtained using a variety of test results or sources of data (i.e., data classes), including at least one of an MDRO gene test 904 applied to the sample 902 and an identification and antibiotic susceptibility test 906 performed on bacterial isolates 908 from the sample 902. The MDRO gene test 904 may result in detection of hundreds of MDRO genes. Together, results from the MDRO gene test 904 and/or the identification and antibiotic susceptibility test 906 may be used to generate a resistome profile for each bacterial isolate of the subject as described hereinabove. The resistome profile(s) may be stored in database 910. As also described hereinabove, additional sample data 912 associated with the sample from the subject, including, but not limited to, information associated with resistance, phenotype, patient history, and metadata, also may be included in the resistome profile(s) and/or stored in database 910. As shown in FIG. 9, the information 912 associated with the sample may be obtained from facility 914 (e.g., a hospital). In some embodiments, in silico profiles may be created from well-documented reference organisms in outbreaks from individual hospitals or countries.

According to some embodiments, analysis engine 916 accesses the resistome profile(s) and/or other data in database 910 to generate any outcome (e.g., a resistome profile, infection state, or infection outbreak classification) described herein. For example, FIG. 9 lists some information that may be communicated to a user using interface 918. As non-limiting examples, the user may use the interface to interact with analysis engine 916 and database 910, including, but not limited to, identifying a resistome profile in database 910 that, for example, meets a parameter according to a search of database 910, viewing a history of a resistome profile in database 910, analyzing trends among resistome profiles in database 910, obtaining and/or transmitting a resistome profile in database 910, ascertaining a prevalence of a resistome profile in database 910, and obtaining and/or transmitting an indication of an active alert and/or report.

As shown in FIG. 9, a report 920 and/or an alert 922 may be communicated to facility 914. For example, a potential for an outbreak at a facility may be determined based on application of analysis engine 916 to the resistome profiles stored in database 910. The report 920 and/or alert 922 may include information indicating the potential for an outbreak at facility 914 or another facility.

Information provided by facility 914 may be communicated back to analysis engine 916 and database 910. As shown in block 924, the platform may provide a capability for facility 914 to interact with analysis engine 916 by sharing real-time, dynamic data and aggregates.

The generation and assignment of a "type" to indicate the uniqueness of each pattern (e.g., the Unique Profile No. of the profile uniqueness identifier) may be challenging when varied test results or sources of data (i.e., data classes) are involved. Current data classes may include, but are not limited to, gene test (e.g., MDRO detection) results, resistome results, identification and antibiotic susceptibility test results, sequencing results, in silico results, mass spectrometry (e.g., MALDI-TOF™) results, phenotype results, and sample metadata. Any given sample for which a resistome profile is generated may have results from one or more of these data classes.

According to some embodiments, comparison of two or more resistome profiles requires that the type of each resistome profile must be derived from the same data classes. For example, if a first sample has only resistome results and a second sample has only MDRO gene detection and identification and antibiotic susceptibility test results, both samples may be assigned resistome profiles, but the types associated with those profiles may be different. Instead of just a numeric identifier, the types for each sample may be expressed in terms of the data class. Some non-limiting examples of data class codes are shown below in TABLE 11:

TABLE 11

| Test Results/Sources of Data | Data Class Code |
|---|---|
| Antibiotic Susceptibility Test Results | A |
| Gene Test Results | G |
| Resistome Results | R |
| Sequencing Results | S |

For example, TABLE 12 shows two examples of resistome profiles for the same sample according to some embodiments. Ex. 12A only requires a numeric type, but Ex. 12B expresses type in terms of the underlying tests.

TABLE 12

| | Resistome Profiles | | | |
|---|---|---|---|---|
| | Pattern | | Profile Uniqueness | |
| Ex. | Organism ID Phenotype | Resistance Genes | Type | $N^{th}$ Member of Type |
| 12A | K1:CRE:KPC_NDM | | 2-5 | |
| 12B | K1:CRE:KPC_NDM | | G2-15_R5-9_A6-4_S19-2 | |

Although Ex. 12A and Ex. 12B share the same pattern, Ex. 12B expresses multiple profile uniqueness identifiers linked to the underlying tests or sources of data according to some embodiments. For Ex. 12A, the pattern (K1:CRE:KPC_NDM) is compared to known patterns, for example, in a database and according to a similarity metric, assigned a profile uniqueness identifier of 2-5, indicating that the pattern has already been assigned Unique Profile No. 2 and has been observed five times in total (i.e., four known patterns in the database share this pattern or a sufficiently similar pattern). For Ex. 12B, the same pattern (K1:CRE:KPC_NDM) may compared to known patterns, for example, even in the same database, except that the comparison depends on profiles with the same type. Thus, the pattern of Ex. 12B is compared to known patterns with the same data classes.

For example, the pattern of Ex. 12B was obtained at least in part from gene test results and therefore may be compared to known patterns also obtained at least in part from gene test results, according to a similarity metric, and assigned a profile uniqueness identifier component G2-15, indicating that, among sufficiently similar patterns obtained at least in part from gene test results, Ex. 12B is being assigned Unique Profile No. 2 and has appeared fifteen times in the database.

The pattern of Ex. 12B also was obtained at least in part from resistome results, antibiotic susceptibility test results, and sequencing results and therefore may be compared to known patterns respectively obtained at least in part from resistome results, antibiotic susceptibility test results, and sequencing results, according to one or more similarity metrics. Thus, Ex. 12B may be assigned the profile uniqueness identifier component R5-9, indicating that, among sufficiently similar patterns obtained at least in part from resistome results, Ex. 12B is being assigned Unique Profile No. 5 and has appeared nine times in the database. Ex. 12B also may be assigned the profile uniqueness identifier component A6-4, indicating that, among sufficiently similar patterns obtained at least in part from antibiotic susceptibility test results, Ex. 12B is being assigned Unique Profile No. 6 and has appeared four times in the database. Ex. 12B further may be assigned the profile uniqueness identifier component S19-2, indicating that, among sufficiently similar patterns obtained at least in part from sequencing results, Ex. 12B is being assigned Unique Profile No. 6 and has appeared only once before in the database.

In another example, TABLE 13 shows two examples of partial resistome profiles according to some embodiments.

TABLE 13

| Ex. | Resistome Profile |
|---|---|
| 13A | ::KPC_NDM:G2-15_R5-9_A6-4_S19-2 |
| 13B | ::KPC_NDM:G3-2 |

While the identity and the phenotype of the organism are not shown, both Ex. 13A and Ex. 13B have the same key resistance genes KPC and NDM. Ex. 13A has gene test, resistome, antibiotic susceptibility test, and sequencing results, but Ex. 13B has only gene test results. According to some embodiments, it need not matter that Ex. 13B has no resistome, antibiotic susceptibility test, or sequencing results, as long as Ex. 13A and Ex. 13B are compared on only common data classes (i.e., gene test results).

According to some embodiments, a resistome profile may be formatted as:

Species ID:Phenotype:Positive Genes: [Testtype]Subtypenumber-Count_[Testtype]Subtypenumber-Count_[Testtype]Subtypenumber-Count Examples of test types in use are A17 (antibiotic susceptibility test or AST with 17 antibiotics, as shown below in TABLE 14) and R70 (i.e., Resistome Test with 70 target genes, as shown below in TABLE 15); however, the above format may be modified, for example, to be re-ordered or to include fewer or additional tests, target genes, and/or antibiotics.

According to some embodiments, a phenotype in a resistome profile may be determined according to the antibiotic susceptibility test rules defined in TABLE 14:

TABLE 14

| Phenotype | AST Rule |
|---|---|
| CRE | [Enterobacteriaceae] && ( <Imipenem> \|\| <Meropenem> ) |
| CR-P.aeru | [Pseudomonas] && ( <Imipenem> \|\| <Meropenem> ) |
| MDR-Acin | var count=0;if ( <Imipenem> \|\| <Meropenem> ) count++;if (<Piperacillin> ) count++;if ( <Amikacin> \|\| <Gentamicin> \|\| <Tobramycin> ) count++; if ( <Ciprofloxacin> \|\| <Levofloxacin> ) count++; if ( <Ampicillin> ) count++; ([Acinetobacter] && count>2) |
| CR-GNB | [GNB] && ( <Imipenem> \|\| <Meropenem> ) |
| CephR-GNB | [GNB] && ( <Ceftazidime> \|\| <Ceftriaxone> \|\| <Cefotaxime> \|\| <Cefepime> ) |
| S-GNB | [GNB] && !( <Imipenem> \|\| <Meropenem> \|\| <Ceftazidime> \|\| <Ceftriaxone> \|\| <Cefepime> ) |

According to some embodiments, a positive gene in a resistome profile may be determined according to the Resistome Test priorities defined in TABLE 15:

TABLE 15

| Target Genes | Priority | Genotype Code |
|---|---|---|
| KPC-1 | 1 | KPC1 |
| NDM-1 | 2 | NDM1 |
| VIM-1 | 3 | VIM1 |
| VIM-2 | 4 | VIM2 |
| VIM-5 | 5 | VIM5 |
| VIM-13 | 6 | VIM13 |
| IMP-1 | 7 | IMP1 |
| IMP-2 | 8 | IMP2 |
| IMP-5 | 9 | IMP5 |
| SME-1 | 10 | SME1 |
| IMI-1 | 11 | IMI1 |
| NMC-A | 12 | NMCA |
| OXA-2 | 13 | OXA2 |
| OXA-10 | 14 | OXA10 |
| OXA-18 | 15 | OXA18 |
| OXA-23 | 16 | OXA23 |
| OXA-24 | 17 | OXA24 |
| OXA-45 | 18 | OXA45 |
| OXA-48 | 19 | OXA48 |
| OXA-50 | 20 | OXA50 |
| OXA-51 | 21 | OXA51 |
| OXA-54 | 22 | OXA54 |
| OXA-55 | 23 | OXA55 |
| OXA-58 | 24 | OXA58 |
| OXA-60 | 25 | OXA60 |
| OXA-62 | 26 | OXA62 |
| CTX-M-1 | 27 | CTXM1 |
| CTX-M-2 | 28 | CTXM2 |
| CTX-M-8/25 | 29 | CTXM8 |
| CTX-M-9 | 30 | CTXM9 |
| VEB-1 | 31 | VEB1 |
| PER-1 | 32 | PER1 |
| GES-1 | 33 | GES1 |
| BES-1 | 34 | BES1 |
| TLA-1 | 35 | TLA1 |

TABLE 15-continued

| Target Genes | Priority | Genotype Code |
|---|---|---|
| SFC-1 | 36 | SFC1 |
| SHV-G238S&E240K | 37 | SHV4 |
| SHV-G238S&E240 | 38 | SHV2 |
| SHV-G238&E240K | 39 | SHV3 |
| SHV-G156D | 40 | SHV6 |
| TEM-G238S&E240K | 41 | TEM10 |
| TEM-G238S&E240 | 42 | TEM8 |
| TEM-G238&E240K | 43 | TEM9 |
| TEM-R164H | 44 | TEM4 |
| TEM-R164C | 45 | TEM5 |
| TEM-R164S | 46 | TEM6 |
| TEM-E104K | 47 | TEM2 |
| SHV-G238&E240(WT) | 48 | SHV1 |
| SHV-G156 (WT) | 49 | SHV5 |

TABLE 15-continued

| Target Genes | Priority | Genotype Code |
|---|---|---|
| TEM-G238&E240(WT) | 50 | TEM7 |
| TEM-R164(WT) | 51 | TEM3 |
| TEM-E104(WT) | 52 | TEM1 |
| BEL-1 | 53 | BEL1 |
| GIM-1 | 54 | GIM1 |
| SPM-1 | 55 | SPM1 |
| DHA-1 | 56 | DHA1 |
| FOX-1 | 57 | FOX1 |
| SIM-1 | 58 | SIM1 |
| ACC-1 | 59 | ACC1 |
| ACC-3 | 60 | ACC3 |
| ACT-1 | 61 | ACT1 |
| ACT-5 | 62 | ACT5 |
| MIR-1 | 63 | MIR1 |
| MOX-1 | 64 | MOX1 |
| MOX-5 | 65 | MOX5 |
| CMY-1 | 66 | CMY1 |
| CMY-2 | 67 | CMY2 |
| CFE-1 | 68 | CFE1 |
| CMY-47 | 69 | CMY47 |
| CMY-70 | 70 | CMY70 |

Each unique combination of positive values for a test type is assigned a sequential subtype number. In the example below in TABLE 16, using the Resistome Test, a third unique combination of positive Resistome gene results was found and therefore assigned the number 3. For the AST result, a second unique combination was observed and therefore assigned the number 2. Count is the number of occurrences across the database of that particular subtype number at the time the type is assigned. In the example below, both the Resistome and AST subtypes were the first occurrence.

TABLE 16

| Species | Phenotype | Resistance Genes | Unique Subtype No. RXX | Unique Subtype No. AXX | No. of Organisms (Count) RXX | No. of Organisms (Count) AXX | Example Resistome Profile |
|---|---|---|---|---|---|---|---|
| K. pneumoniae | CRE | SHV-G238&E240 (WT) and TEM-R164H | 3 | 2 | 1 | 1 | K1:CRE:KPC1_SHV1_TEM4: [RXX]3-1_[AXX]2-1 |

Communication of Outcomes

In some embodiments, systems, apparatus, and/or methods communicate value-added information to stakeholders (e.g., a facility agent, a physician, an infection control professional, or a public health agency) concerning a resistome profile, an infection state, and/or an outbreak classification.

According to some embodiments, an individual resistome profile is interrogated for valuable clinical therapeutic insights regarding diagnosis, clinical significance, and treatment decisions. Execution of processor-executable instructions may lead a processor to interrogate a computer database based on a resistome profile and, if a match is identified, indicate a level of clinical significance of the match (a similarity metric above a threshold). For example, a K1:CRE:KPC:1-1 profile (*K. pneumonia* with a carbapenem-resistant phenotype and a KPC plasmid gene) may be ranked in a database as a more critical infection or colonization than an E1:ESBL:C1:1-1 profile (*E. coli* with an ESBL phenotype and a CTX group 1 genotype). For example, a stakeholder may be informed that, based on a resistome profile that indicates an organism with both a VIM or IMP metalloproteinase carbapenem genotype and an ESBL genotype, the respective subject may not be responsive to Aztreonam, one of a few choices for treating the infection.

Some embodiments are configured to provide guidance regarding in silico data, such as published results from expert observations and research in the field. In silico data may be used to augment unique resistome profiles by comparing them to well-characterized reference strains. For example, an in silico comparison may be made between the clone ST258 and various KPC subtypes such as KPC-2 or KPC-3 that are geographically predominant, known to come from local facilities, etc.

In addition to facilitating rapid diagnosis and/or treatment decisions, systems, apparatus, and methods may be configured to indicate that there is a potential outbreak or common source of infection according to some embodiments. Using resistome profiles, systems, apparatus, and methods may be configured to search geographical and/or facility-based demographic data. Systems, apparatus, and methods may be configured to generate a map of a geographical area or facility (including, but not limited to, ICU rooms) where various resistome profiles have been identified, to classify the facility according to micro-geographic matches. The example resistome profiles may be used to provide statistical data and tracking data. In some embodiments, systems, apparatus, and methods automatically transmit and/or display an alert or report. For example, an alert or report may be transmitted or displayed when resistome profiles K1:CRE:KPC:1-1, K1:CRE:KPC:1-2, and K1:CRE:KPC:1-3 have been identified for subjects in a single facility (including, but not limited to, an individual ICU). The alert or report may include at least one of a resistome profile, an infection state, a classification, a map, statistical data, and tracking data.

In some embodiments, information indicating an outcome (e.g., a resistome profile, infection state, or potential outbreak classification) may be stored or output via a network or displayed to a user. For example, information indicating a resistome profile may be compressed, stored, transmitted, applied, and/or displayed as one or more numbers, textual symbols, graphical images, or some combination thereof. In some embodiments, a graphical image includes, but is not limited to, a two-dimensional code (e.g., a QR code), a tube graph, and an epidemiology star chart. In further embodiments, alerts or reports as to an outcome also may be compressed, stored, transmitted, applied, and/or displayed as one or more numbers, textual symbols, graphical images, or some combination thereof. In addition, alerts or reports as to an outcome may be accompanied by audio or tactile output, depending on the user device.

As shown in FIG. 9, a user and/or facility may communicate over interface 918 to identify a resistome profile in database 910 that, for example, meets a parameter according to a search of database 910, view a history of a resistome profile in database 910, analyze trends among resistome profiles in database 910, obtain and/or transmit a resistome profile from database 910, ascertain a prevalence of a resistome profile in database 910, and obtain and/or transmit an indication of an active report 920 and/or an alert 922. The report 920 and/or alert 922 may include information indicating the potential for an outbreak at facility 914 or another facility.

Figure 10B:
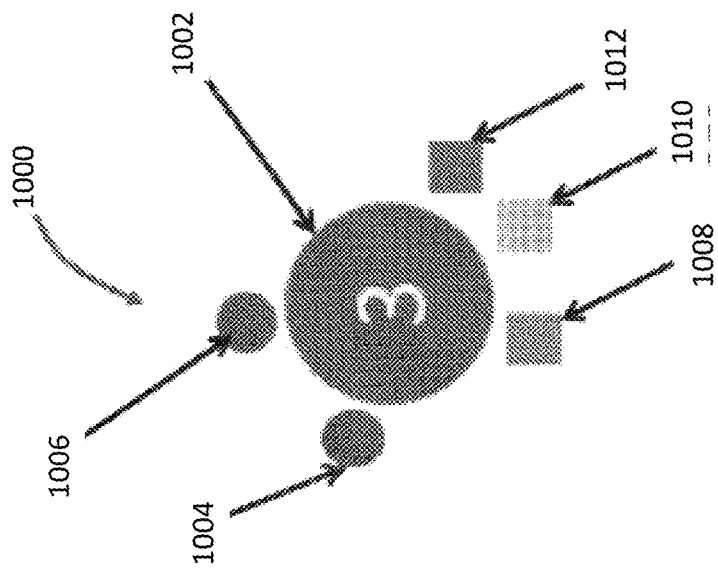
FIGS. 10A and 10B illustrate graphical representations of resistome profiles in accordance with some embodiments.
Figure 10A:
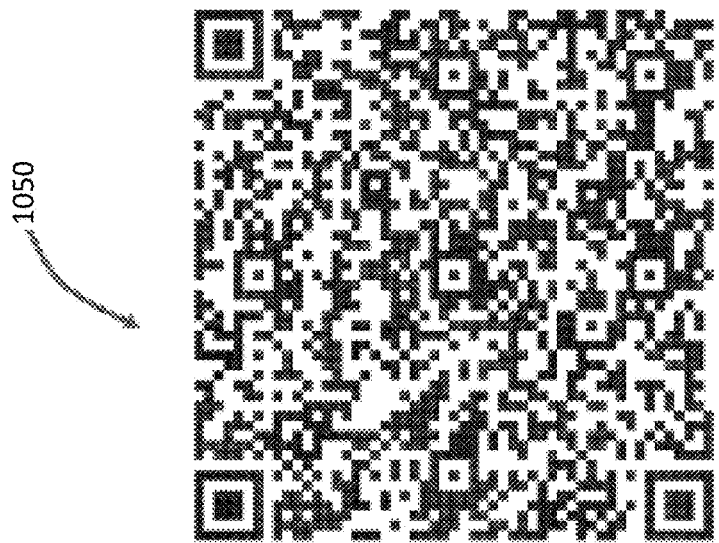

FIG. 10A illustrates a non-limiting example of a graphical representation of a resistome profile 1000 according to some embodiments. In this example, resistome profile E1:KPC_O48:EPN_MPN_CTD:24-3 is represented. A large green circle 1002 represents the organism identification code E1 (indicating *E. coli*), the small red circle 1004 and small purple circle 1006 respectively represent the presence of KPC and OXA-48 resistance genes while the blue square 1008, yellow square 1010 and brown square 1012 respectively represent resistance to the antibiotics EPN (Ertapenem), MPN (Meropenem), and CTD (Ceftazidime). The number "3" in circle 1002 indicates three occurrences of organisms in a known database with this pattern. The graphical display may be further configured to display any other database information not included in the pattern or profile uniqueness identifier.

FIG. 10B illustrates an alternative non-limiting example of a graphical representation of a resistome profile using a QR code 1050 according to some embodiments. The QR code represents a resistome profile for a *K. pneumoniae* organism with a CRE phenotype and resistance genes VIM and CTX-M-1, that is non-susceptible to Doripenem, Imipenem and Meropenem, and assigned a profile uniqueness code indicating that it is Unique Profile #34 with two other known organisms in the database with this pattern. The QR code may also be coded to include any other database information not included in the pattern or profile uniqueness identifier.

In some embodiments, an indication of a classification of a population (e.g., a facility) as to a potential for infection outbreak may be displayed using a graphical representation similar to the non-limiting examples shown in FIGS. 10A and 10B.

In some embodiments, systems, apparatus, and/or methods facilitate choosing a naming convention that, for example, is consistent with a different classification system, thus reducing the need for translation, and thereby saving memory and processing time. In some embodiments, the codes used to generate patterns in a first database of known patterns differ from the codes used to generate patterns in a second database of known patterns. The codes may differ by at least one of the organism identification code, the phenotype code, the genotype code, and the susceptibility code. At least one conversion table may correlate the codes for the first database to the codes for the second database. According to some embodiments, the systems, apparatus, and methods described herein are configured to apply at least one conversion table to known patterns in the first or second database in order to perform any comparison described herein.

The ability to view additional or varied information may be set by a user as a preference on a customized basis, or the information may be hidden and made available based on a request or selection from a user according to some embodiments. For example, a display interface may be configured such that the user can make a selection on a short form name or symbol to expand a field or open a new window on the display that provides detailed antibiotic resistance data or other diagnostically useful information for a subject sample. For example, in TABLE 17, the differences in minimum inhibitory concentration (MIC) results for two isolate species are provided.

TABLE 17

| | Isolate No. | |
|---|---|---|
| | 850707 MIC Value (mg/L) | 850793 MIC Value (mg/L) |
| Amikacin | 32 | 32 |
| Amoxicillin Clavulanic Acid | 16 | 16 |
| Ampicillin | 32 | 32 |
| Cefepime | 16 | 16 |
| Ceftazidime | 16 | 128 |
| Ceftazidime Clavulanic | 16 | 128 |
| Colistin/TWEEN | 0.12 | 0.12 |
| Doripenem | 32 | 4 |
| Ertapenem | 6 | 1 |
| Imipenem | 2 | 8 |
| Levofloxacin | 1 | 0.5 |
| Meropenem | 32 | 8 |
| Piperacillin Tazobactam | 64 | 128 |
| Teicoplanin | — | — |
| Tigecycline | 2 | 1 |
| Vancomycin | — | — |

In TABLE 18, the isolates are numbered and linked to an isolate species (*K. pneumoniae*); resistome profiles including the species (K1), phenotype (CRE), genotype (IMP and C1), and profile uniqueness identifiers indicating sequential unique patterns compared to an associated database (1-1 and 2-1, respectively); Acuitas MDRO Gene Test results (IMP(A) and CTX-M(A)); and reported genotypes listed in rank order of clinical importance (IMP-26, CTX-M-15, and SHV-28(u), and IMP-4, CTX-M-15, SHV-1(b), and TEM, respectively). The trailing "1s" in the assigned resistome profiles (i.e., the second digit of each profile uniqueness identifier) reflect the first occurrences of these patterns/profiles derived based on data collected from subject sample measurements. In this example, the tests are not designed to detect SHV, TEM, ACT/MIR, CMY-2, DHA-1, ACT-16, or VEB-1.

TABLE 18

| Isolate No. | Isolate Species | Resistome Profile | Acuitas MDRO Gene Test Results | Reported Genotype |
|---|---|---|---|---|
| 850707 | *K. pneumoniae* | K1:CRE:IMP_C1:1-1 | IMP(A) and CTX-M(A) | IMP-26, CTX-M-15, and SHV-28(u) |
| 850793 | *K. pneumoniae* | K1:CRE:IMP_C1:2-1 | IMP(A) and CTX-M(A) | IMP-4, CTX-M-15, SHV-1(b), and TEM |

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments may be implemented in any of numerous ways. For example, implementations of the subject matter described herein may be realized in digital electronic circuitry, integrated circuitry, specially designed ASICs (application specific integrated circuits), computer hardware, firmware, software, and/or combinations thereof. When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital assistant (PDA), a smart phone, or any other suitable portable or fixed electronic device.

Also, a computer may have one or more input and output devices. These devices may be used, among other things, to present a user interface. Examples of output devices that may be used to provide a user interface include printers or display screens, such as CRT (cathode ray tube) or LCD (liquid crystal display) monitors, for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible format. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. As used herein, "machine-readable medium" refers to any computer program product or apparatus (e.g., a magnetic disc, an optical disk, memory, a Programmable Logic Device (PLD)) used to provide machine instructions and/or data to a programmable processor, including a machine-readable medium that receives machine instructions as a "machine-readable signal," which includes any signal used to provide machine instructions and/or data to a programmable processor.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

The invention claimed is:

1. A system comprising:
an assay device configured to receive a first sample including an organism the first sample associated with a patient, the assay device further configured to generate first data representative of at least one measure of antibiotic resistance of an organism by processing the first sample to extract genetic information associated with the organism; and
a processor communicatively coupled to the assay device, the processor configured to:
receive, the first data from the assay device;
identify the organism based on at least the first data;
determine at least one of an antibiotic susceptibility phenotype, an identity of an antibiotic resistance gene, and an antibiotic to which the organism is non-susceptible based on at least the first data;
generate a first pattern associated with the first sample, the first pattern comprising:
an organism identification code indicating the organism identified based on the first data; and
at least one of:
a phenotype code indicating the antibiotic susceptibility phenotype determined from the first data;
a genotype code indicating the identity of the antibiotic resistance gene determined from the first data; and
a susceptibility code indicating the antibiotic to which the organism is non-susceptible determined from the first data;
compare the first pattern to at least one known pattern;
calculate a degree of similarity between the first pattern and the at least one known pattern;
generate a first resistome profile based on at least the first pattern; and
automatically generating a real-time alert when the degree of similarity is above a threshold indicating at least one of an outbreak or a common source of infection such that the patient can be contained.

2. The system of claim 1, wherein the first pattern comprises a plurality of genotype codes, each genotype code indicating the identity of a different antibiotic resistance gene.

3. The system of claim 1, wherein calculating the degree of similarity between the first pattern and the at least one known pattern includes:
calculating a uniqueness code based on the degree of similarity between the first pattern and the at least one known pattern; and
calculating a repetition index indicating a number of known patterns from the at least one known pattern which the first pattern matches with a degree of similarity above the threshold.

4. The system of claim 1, wherein the processor is further configured to compare the first pattern to the at least one known pattern by applying a similarity metric to the first pattern and the at least one known pattern to calculate the degree of similarity above the threshold between the first pattern and the at least one known pattern.

5. The system of claim 1, wherein the first sample is obtained from at least one of an anal swab, a rectal swab, a skin swab, nasal swab, wound swab, stool, blood, plasma, serum, urine, sputum, respiratory lavage, and cerebrospinal fluid.

6. The system of claim 1, wherein the first data representative of the at least one measure of antibiotic resistance of the organism from the first sample comprises data representative of at least one of a type of gene, a gene sequence, a gene family, a DNA sequence, a single-nucleotide polymorphism, a type of nucleic acid, a type of protein, and a protein expression.

7. The system of claim 1, wherein the first resistome profile further comprises metadata associated with at least one of the first sample and a first subject from which the first sample was obtained.

8. The system of claim 1, wherein the first data representative of the at least one measure of antibiotic resistance of the organism from the first sample comprises data representative of at least one measure of a susceptibility test performed on a first bacterial isolate from the first sample.

9. The system of claim 1, further comprising a graphical display communicatively coupled to the processor, the processor further configured to display, via the graphical display, the first resistome profile using a graphical representation, the graphical representation comprising at least one of:

a quick response (QR) code;
a tube graph; and
an epidemiology star chart.

10. The system of claim 1, wherein the first data representative of the at least one measure of antibiotic resistance of the organism from the first sample is collected from at least one measurement of a first bacterial isolate from the first sample and indicates at least one of an antibiotic resistance of the first bacterial isolate and an antibiotic susceptibility of the first bacterial isolate.

11. The system of claim 1, wherein the at least one known pattern is derived from measurement data associated with a second bacterial isolate from a second sample obtained from at least one of a colonized subject and an infected subject, the colonized patient having tested positive for at least one drug-resistant organism, and the infected patient having at least one of a central line blood infection, ventilator associated pneumonia, a urinary tract infection, and a surgical site infection, the measurement data indicating at least one of an antibiotic resistance of the first bacterial isolate and an antibiotic susceptibility of the first bacterial isolate.

12. The system of claim 1, wherein the first data representative of the at least one measure of antibiotic resistance of the organism from the first sample indicates at least one of a genome sequence, a minimum inhibitory concentration for an antibiotic, and MALDI-TOF data.

13. The system of claim 1, wherein the first data representative of the at least one measure of antibiotic resistance of the organism from the first sample comprises in silico data from a reference organism involved in an outbreak.

14. A method, comprising:
receiving a first sample including an organism at an assay device, the first sample associated with a geographic location;
processing, by the assay device, the first sample to extract genetic information associated with the organism;
generating, based on the genetic information, first data representative of at least one measure of antibiotic resistance of the organism;
identifying the organism based on at least the first data;
determining at least one of an antibiotic susceptibility phenotype, an identity of an antibiotic resistance gene, and an antibiotic to which the organism is non-susceptible based on at least the first data;
generating a first pattern associated with the first sample, the first pattern comprising:
an organism identification code indicating the organism identified based on the first data; and
at least one of:
a phenotype code indicating the antibiotic susceptibility phenotype determined from the first data;
a genotype code indicating the identity of the antibiotic resistance gene determined from the first data; and
a susceptibility code indicating the antibiotic to which the organism is non-susceptible determined from the first data;
comparing the first pattern to at least one known pattern;
calculating a degree of similarity between the first pattern and the at least one known pattern;
generating a first resistome profile based on at least the first pattern; and
automatically generating a real-time alert when the degree of similarity is above threshold, the real-time alert indicating the presence of an antibiotic-resistant organism at the geographic location such that at least one of the geographic location or a patient associated with the geographic location can be at least one of treated, disinfected, or isolated.

15. The method of claim 14, wherein the first pattern comprises a plurality of genotype codes, each genotype code indicating the identity of a different antibiotic resistance gene.

16. The method of claim 14, wherein calculating the degree of similarity between the first pattern and the at least one known pattern includes:
calculating a uniqueness code based on the degree of similarity between the first pattern and the at least one known pattern; and
calculating a repetition index indicating a number of known patterns from the at least one known pattern which the first pattern matches with a degree of similarity above the threshold.

17. The method of claim 14, wherein comparing the first pattern to the at least one known pattern comprises applying a similarity metric to the first pattern and the at least one known pattern to calculate the degree of similarity above the threshold between the first pattern and the at least one known pattern.

18. The method of claim 14, wherein the first sample is obtained from at least one of an anal swab, a rectal swab, a skin swab, nasal swab, wound swab, stool, blood, plasma, serum, urine, sputum, respiratory lavage, and cerebrospinal fluid.

19. The method of claim 14, wherein the first data representative of the at least one measure of antibiotic resistance of the organism from the first sample comprises data representative of at least one of a type of gene, a gene sequence, a gene family, a DNA sequence, a single-nucleotide polymorphism, a type of nucleic acid, a type of protein, and a protein expression.

20. The method of claim 14, wherein the first resistome profile further comprises metadata associated with at least one of the first sample and a first subject from which the first sample was obtained.

21. The method of claim 14, wherein the first data representative of the at least one measure of antibiotic resistance of the organism from the first sample comprises data representative of at least one measure of a susceptibility test performed on a first bacterial isolate from the first sample.

22. The method of claim 14, further comprising displaying the first resistome profile using a graphical representation, the graphical representation comprising at least one of:
a quick response (QR) code;
a tube graph; and
an epidemiology star chart.

23. The method of claim 14, wherein the first data representative of the at least one measure of antibiotic resistance of the organism from the first sample is collected from at least one measurement of a first bacterial isolate from the first sample and indicates at least one of an antibiotic resistance of the first bacterial isolate and an antibiotic susceptibility of the first bacterial isolate.

24. The method of claim 14, wherein the at least one known pattern is derived from measurement data associated with a second bacterial isolate from a second sample obtained from at least one of a colonized subject and an infected subject, the colonized patient having tested positive for at least one drug-resistant organism, and the infected patient having at least one of a central line blood infection, ventilator associated pneumonia, a urinary tract infection, and a surgical site infection, the measurement data indicating at least one of an antibiotic resistance of the first bacterial isolate and an antibiotic susceptibility of the first bacterial isolate.

25. The method of claim 14, wherein the first data representative of the at least one measure of antibiotic resistance of the organism from the first sample indicates at least one of a genome sequence, a minimum inhibitory concentration for an antibiotic, and MALDI-TOF data.

26. The method of claim 14, wherein the first data representative of the at least one measure of antibiotic resistance of the organism from the first sample comprises in silico data from a reference organism involved in an outbreak.

* * * * *